(12) United States Patent
Nelson et al.

(10) Patent No.: US 6,709,818 B1
(45) Date of Patent: Mar. 23, 2004

(54) METHODS OF DIAGNOSING AND TREATING HEPATIC CELL PROLIFERATIVE DISORDERS

(75) Inventors: William G. Nelson, Towson, MD (US); Xiaohui Lin, Baltimore, MD (US); Julia C. Tchou, Baltimore, MD (US); Jila Bakker, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/687,246

(22) Filed: Oct. 12, 2000

Related U.S. Application Data

(60) Provisional application No. 60/159,168, filed on Oct. 13, 1999.

(51) Int. Cl.[7] .............................. C12Q 1/68; C12P 19/34; C07H 21/04
(52) U.S. Cl. ..................... 435/6; 435/91.1; 435/91.2; 536/23.1; 536/24.3; 536/24.31; 536/24.33
(58) Field of Search .......................... 435/6, 91.1, 91.2; 536/23.1, 23.5, 24.3, 24.31, 24.33

(56) References Cited

U.S. PATENT DOCUMENTS

| | | | |
|---|---|---|---|
| 5,552,277 A | * | 9/1996 | Nelson et al. .................. 435/6 |
| 5,786,146 A | | 7/1998 | Herman et al. |
| 5,891,628 A | | 4/1999 | Reeders et al. |
| 6,017,704 A | * | 1/2000 | Herman et al. .................. 435/6 |
| 6,200,756 B1 | | 3/2001 | Herman et al. |

FOREIGN PATENT DOCUMENTS

WO   WO 97/46706 A1   12/1997

OTHER PUBLICATIONS

De Oliveira e Silva et al., Arquivos De Gastroenterologia, vol. 27, 1990, English abstract only.*
Imai et al., Carcinogenesis, vol. 18, pp 545–551, 1997.*
Steinmetz et al., Carcinogenesis, vol. 19, pp 1487–1494, 1998.*
Steinmetz, K.L., et al.; Hypomethylation of the rat glutathione S–transferase pi (GSTP) promoter region isolated from methyl–deficient livers and GSTP positive liver neoplasms; Carcinogenesis, 1988, vol. 19, No. 8, pp. 1487–1494; see whole document.
Jhaveri, M.S., et al.; Methylation–mediated regulation of the glutathione–S–transferase P1 gene in human breast cancer cells; Gene, 1998, vol. 210, pp. 1–7; see whole document.
Copy of PCT International Search Report Document for PCT/US00/28427 (4 pages).
Tchou, Julia C. et al., "GSTP1 CpG Island DNA Hypermethylation in Hepatocellular Carcinomas", International Journal of Oncology 16, 2000 pp. 663–676.

* cited by examiner

*Primary Examiner*—Gary Benzion
*Assistant Examiner*—Jehanne E Souaya
(74) *Attorney, Agent, or Firm*—Gray Cary Ware & Freidenrich, LLP; Lisa A. Haile; Emanuel J. Vacchiano

(57) ABSTRACT

Provided are methods and compositions useful for the diagnosis, prognosis and treatment of hepatic cellular proliferative disorders. The methods include the modulation or analysis of hypemethylated glutathione-S-transferase nuleic acid sequence in hepatic samples and biological fluids.

35 Claims, 5 Drawing Sheets

A   Southern Analysis

B   Northern Analysis

500
METHODS OF DIAGNOSING AND TREATING HEPATIC CELL PROLIFERATIVE DISORDERS

CROSS REFERENCE TO RELATED APPLICATIONS

The present application claims priority under 35 U.S.C. §119(e)(1) to U.S. Provisional Application No. 60/159,168, filed Oct. 13, 1999, the disclosure of which is incorporated herein by reference.

STATEMENT REGARDING FEDERALLY SPONSORED RESEARCH

The U.S. Government may have certain rights in this invention pursuant to Grant No.: CA58236 and CA70196 by the National Institute of Health (NIH).

FIELD OF THE INVENTION

The present invention relates generally to the diagnosis of cancer and specifically to identification of a hypermethylated glutathione-S-transferase (GSTP1) gene as a diagnostic indicator of hepatic cell proliferative disorders.

BACKGROUND

Hepatocellular carcinoma (HCC) constitutes one of the most common life-threatening cancers in world. Most HCC cases arise in the setting of chronic hepatitis virus infection. Dietary carcinogens, such as alflatoxin B1, likely also contribute to hepatic carcinogenesis. Glutathione S-transferases (GSTs) may help defend normal hepatocytes against a variety of potentially promutagenic stresses, including reactive oxygen species associated with chronic hepatic inflammation, and reactive electrophilic compounds associated with the hepatic metabolism of dietary carcinogens. Therapeutic elevation of the expression of GSTs and other carcinogen detoxification enzymes has been demonstrated to attenuate hepatic carcinogenesis in animal models. Oltipraz, an inducer of carcinogen detoxification enzyme expression in hepatocytes, is currently under development as a chemoprotective agent for human HCC.

In higher order eukaryotes DNA is methylated only at cytosines located 5' to guanosine in the CpG dinucleotide. This modification has important regulatory effects on gene expression, especially when involving CpG rich areas, known as "CpG islands," located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosome of females. Abberant methylation of normally unmethylated CpG islands has been described as a frequent event in immortalized and transformed cells, and has been associated with transcriptional inactivation of defined tumor suppressor genes in human cancers.

Somatic "CpG island" DNA hypermethylation changes have been frequently detected in human cancer cell genomes. Several tumor suppressor genes, such as Rb, VHL, and p16, have been reported to be inactivated by "CpG island" DNA hypermethylation in different human cancer types. For HCC, changes in DNA methylation at a number of gene loci have been found to frequently accompany carcinogenesis. In one study, somatic "CpG island" hypermethylation affecting E-cadherin was detected in the majority (67%) of human HCC specimens and in many (46%) liver tissues showing chronic hepatitis or cirrhosis. In another study, abnormal DNA methylation changes at several loci along chromosome 16, a chromosome frequently exhibiting allelic losses in HCC, were also detected in HCC DNA and DNA from liver tissues with chronic hepatitis or cirrhosis.

Human cancer cells typically contain somatically altered genomes, characterized by mutation, amplification, or deletion of critical genes. In addition, the DNA template from human cancer cells often displays somatic changes in DNA methylation. However, the precise role of abnormal DNA methylation in human tumorigenesis has not been established. DNA methylases transfer methyl groups from the universal methyl donor S-adenosyl methionine to specific sites on the DNA Several biological functions have been attributed to the methylated bases in DNA The most established biological function is the protection of the DNA from digestion by cognate restriction enzymes. The restriction modification phenomenon has, so far, been observed only in bacteria. Mammalian cells, however, possess a different methylase that exclusively methylates cytosine residues on the DNA, that are 5' neighbors of guanine (CpG). This methylation has been shown by several lines of evidence to play a role in gene activity, cell differentiation, tumorigenesis, X-chromosome inactivation, genomic imprinting and other major biological processes.

A CpG rich region, or "CpG island", has recently been identified at 17p13.3, which is aberrantly hypermethylated in multiple common types of human cancers. This hypermethylation coincides with timing and frequency of 17p losses and p53 mutations in brain, colon, and renal cancers. Silenced gene transcription associated with hypermethylation of the normally unmethylated promoter region CpG islands has been implicated as an alternative mechanism to mutations of coding regions for inactivation of tumor suppressor genes. This change has now been associated with the loss of expression of VHL, a renal cancer tumor suppressor gene on 3p, the estrogen receptor gene on 6q and the H19 gene on 11p.

In eukaryotic cells, methylation of cytosine residues that are immediately 5' to a guanosine, occurs predominantly in CG poor regions. In contrast, discrete regions of CG dinucleotides called CpG islands remain unmethylated in normal cells, except during X-chromosome inactivation and parental specific imprinting where methylation of 5' regulatory regions can lead to transcriptional repression. De novo methylation of the Rb gene has been demonstrated in a small fraction of retinoblastomas, and recently, a more detailed analysis of the VHL gene showed aberrant methylation in a subset of sporadic renal cell carcinomas. Expression of a tumor suppressor gene can also be abolished by de novo DNA methylation of a normally unmethylated 5' CpG island.

Identification of the earliest genetic changes in tumorigenesis is a major focus in molecular cancer research. Diagnostic approaches based on identification of these changes are likely to allow implementation of early detection strategies and novel therapeutic approaches targeting these early changes might lead to more effective cancer treatment.

SUMMARY OF THE INVENTION

The present invention provides for the first time that ability to detect and treat hepatic cell proliferative disorders by detecting a methylated CpG-containing glutathione-S-transferase.

In one embodiment, the invention provides a method for detecting a hepatic cell proliferative disorder by detecting a methylated CpG-containing glutathione-S-transferase (GST) nucleic acid in a hepatic specimen or biological fluid wherein a methylated GST nucleic acid is indicative a hepatic cell proliferative disorder. The method of detecting may include contacting a nucleic acid-containing hepatic specimen or biological fluid with an agent that modifies unmethylated cytosine, amplifying the CpG-containing nucleic acid in the specimen by means of CpG-specific oligonucleotide primers, wherein the oligonucleotide primers distinguish between modified methylated and nonmethylated nucleic acid, and detecting the methylated nucleic acid based on the presence or absence of amplification products produced in during amplification. Alternatively, the detection may be performed by contacting a target nucleic acid in the hepatic specimen or biological fluid with a reagent which detects methylation of the promoter region of the GST when the target nucleic acid is DNA, or wherein the reagent detects the level of GST RNA when the target nucleic acid is RNA, and detecting the GST target nucleic acid, wherein hypermethylation of the promoter of GST DNA, or decreased levels of GST RNA, as compared with the level of GST RNA in a normal cell, is indicative of a GST-associated cell proliferative disorder in hepatic tissue. The GST can be a n family GST (e.g., GSTP1).

In another embodiment, the invention provides a method for detecting a hepatic cell proliferative disorder associated with a glutathione-S-transferase (GST) in a subject by contacting a target nucleic acid in a sample of hepatic tissue or biological fluid from the subject with a reagent which detects the GST, wherein the reagent detects methylation of the promoter region of the GST when the target nucleic acid is DNA, and wherein the reagent detects the level of GST RNA when the target nucleic acid is RNA, and detecting the GST target nucleic acid, wherein hypermethylation of the promoter of GST DNA, or decreased levels of GST RNA, as compared with the level of GST RNA in a normal cell, is indicative of a GST-associated cell proliferative disorder in hepatic tissue.

In yet another embodiment, the inventin provides a method for detecting a hepatic cell proliferative disorder associated with a glutathione-S-transferase (GST) nucleic acid in a subject. The method includes contacting a target cellular component containing a GST nucleic acid with a reagent which reacts with the GST nucleic acid and detecting hypermethylation of the GST nucleic acid, wherein hypermethylation of the GST nucleic acid is indicative of a hepatic cell proliferative disorder.

In another embodiment, the invention provides a method for detecting a hepatic cell proliferative disorder associated with a glutathione-S-transferase (GST) in a subject. The method includes contacting a sample from the subject with a reagent that detects GST polypeptide and comparing the level of GST polypeptide in the sample to a control sample wherein a reduced level in the sample is indicative of a hepatic cell proliferative disorder.

In yet another embodiment, the invention provides a method for treating a hepatic cell proliferative disorder. The method includes contacting a subject in need of such treatment with an agent which increases the expression of a glutathione-S-transferase (GST), thereby treating the hepatic cell proliferative disorder.

In another embodiment, the invention provides a kit useful for the detection of a methylated CpG-containing nucleic acid in a GSTP1 promoter. The kit includes carrier means containing one or more containers having a first container containing a reagent which modifies unmethylated cytosine and a second container containing primers for amplification of the CpG-containing nucleic acid, wherein the primers distinguish between modified methylated and nonmethylated nucleic acid.

In yet another embodiment, the invention provides isolated oligonucteotide primer(s) for detection of a methylated CpG-containing nucleic acid wherein the primer hybridizes with a target polynucleotide sequence having the sequence in the region from about −539 to −239 upstream from GSTP1 transcription start site.

DETAILED DESCRIPTION OF THE INVENTION

Figure 1:
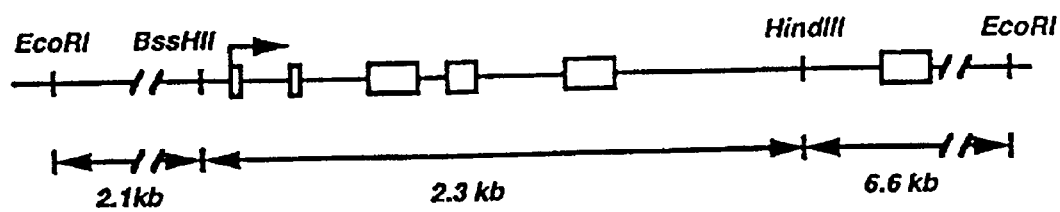
FIG. 1A shows a southern blot analysis of DNA from Hep3B cells treated for 72 hours with different concentrations of 5-azadeoxycytidine (aza-dC).
FIG. 1B shows a northern analysis of GSTP1 mRNA expression by Hep3B cells treated with 5-azadeoxycytidine.
Figure 1:
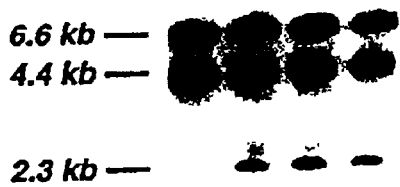
Figure 1:
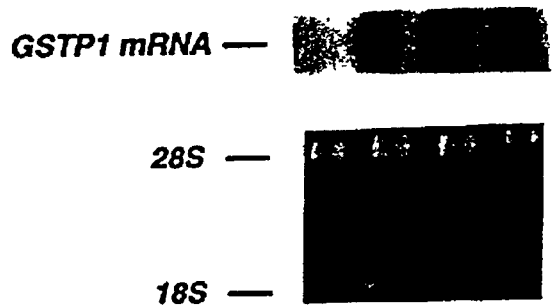

The present invention is based upon the observation that human liver carcinogenesis proceeds via an accumulation of "CpG island" hypermethylation changes at GSTP1 one or both alleles. The discovery that "CpG island" DNA hypermethylation changes affecting GSTP1, located on chromosome 11, are present in at least 85% of HCC cases studied supports the basis of the invention. As described more fully below, liver cancer cells failed to express either GSTP1 mRNA or GSTP1 polypeptides. Similarly, in 19 of 20 HCC cases assessed, HCC cells were devoid of GSTP1 polypeptides detected by immuno-histochemical staining using specific antiserum DNA isolated from liver cancer cells and from the majority of HCC specimens displayed somatic GSTP1 "CpG island" hypermethylation. Genomic sequencing analyses, undertaken to map 5-methyldeoxycytidine ($^{5-m}C$) nucleotides located at the GSTP1 transcriptional regulatory region, indicated that the somatic DNA hypermethylation changes present in HCC DNA consistently affected the gene promoter. These GSTPI1 DNA hypermethylation changes contributed to GSTP1 inactivation in the HCC cells. In addition, treatment of Hep3B HCC cells in vitro with a DNA-methyltransferase inhibitor (e.g., 5-azadeoxycytidine (5-aza-dC)) both reversed GSTP1 "CpG island" hypermethylation and restored GSTP1 expression. The methods described in the present invention allow detection of GSTP1 CpG island hypermethylation affecting one or both maternal and paternal alleles.

GSTs are dimeric enzymes with subunit polypeptides encoded by an array of genes organized into several gene families: $\alpha, \mu, \pi$, and $\theta$. In rat models of HCC, after exposure to an initiating carcinogen, hyperplastic nodules containing liver cells displaying increased expression of the $\pi$- class GST (GST-P) stereotypically appear. This increase in GST-P expression, accompanied by increases in the expression of other carcinogen detoxification enzymes, has been proposed to afford the preneoplastic hepatocytes some protection against ongoing exposure to hepatic carcinogens. Many of the HCCs which ultimately arise in the carcinogen-treated rats continue to express high levels of GST-P. Maintenance of high level expression of GST-P and other carcinogen detoxification enzymes by HCC cells arising in carcinogen-treated rats has been offered as evidence for selection of a carcinogen-resistance phenotype during hepatic carcinogenesis appear. In this model, increases in the expression of carcinogen detoxification enzymes enable transformed hepatocytes to attempt to elude the cytotoxic effects of chronic oxidant or electrophile exposure. Alternatively, inadequate GST expression by normal and preneoplastic hepatocytes has been proposed to render such cells vulnerable to the promutagenic effects of carcinogen exposure that promote neoplastic transformation. In support of this alternative model, most hyperplastic nodules in carcinogen-treated rats fail to progress to HCC, suggesting that increased GST-P expression in preneoplastic hepatocytes may pose a barrier to hepatocellular transformation. Fish species, such as the white suckers (*Catosiomus commersom*), exposed to carcinogenic water pollutants in Lake Ontario develop HCC containing low levels of GSTs. Hepatocytes comprising abnormal liver lesions in rainbow trout (*Onchorhynchus mykiss*) which fail to induce GST expression in response to aflatoxin B1 or 1,2-dimethylbenzanthracene exposure appear prone to develop larger and more expansive liver neoplasms than hepatocytes in abnormal liver lesions with increased GST levels. The concept that lack of GST expression might result in increased vulnerability to carcinogen-induced tumorigenesis is supported by the recent finding that mice carrying disrupted Gstp genes display an increased number of skin tumors following topical exposure to 7,12 dimethylbenzanthracene.

Analyses of GST expression in human HCC cells have not been entirely consistent with the findings of rat HCC model. In three different HCC case studies, high level expression of GSTP1, the human $\pi$-class GST, was reported in only 3 of 12, 9 of 16, and 12 of 31 HCC cases. Moreover, a recent study of the expression of several different GST isoenzymes in HCC specimens from China revealed an overall reduction GST levels in HCC tissues. The decrease in GST levels in HCC tissues was particularly marked in specimens that were found to contain HBV DNA New insights into the molecular pathogenesis of human prostate cancer (PCA) may provide a clue. During human prostatic carcinogenesis, prostatic carcinoma (PCA) cells characteristically fail to express GSTP1 as a consequence of a somatic GSTP1 inactivation. The somatic genome lesion detected most often, methylation of deoxycytidine nucleotides comprising a "CpG island" encompassing the gene promoter, likely causes transcriptional silencing of GSTP1. Somatic GSTP1 DNA hypermethylation changes have been detected in more than 90% of PCA lesions and some 70% of PCA precursor lesions (prostatic intraepithelial neoplasia or "PIN" lesions). Somatic GSTP1 DNA hypermethylation associated with absence of GSTP1 expression has also been reported for breast and renal carcinomas.

The present invention reveals that hypermethylation of the human $\pi$-class glutathione-S-transferase structural gene (GSTP1) positively correlates with hepatic carcinogenesis. Particularly hypermethylation of the promoter region reduces the expression of GSTP1 in liver tissue. This unexpected finding now allows the detection of hepatic tissue cellular proliferative disorders by a simple assay that detects hypermethylation of glutathione-S-transferase sequences (e.g., promoter sequences) either directly, by restriction endonuclease analysis, or indirectly, by detection of GSTP1 mRNA or GSTP1 gene product. In addition, methods of treating hepatic cellular cancers are now possible and include the modulation of hypermethylation of glutathione-S-transferases in the liver. Methods of treatment which focus on replacing the hypermethylated promoter with a non-methylated promoter, for example, are now possible.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous. Expression control sequences include a promoter.

By "promoter" is meant a minimal sequence sufficient to direct transcription, for example, transcription of a glutathione-S-transferase. In recombinant vectors, for example, a promoter includes elements which are sufficient to render promoter-dependent gene expression controllable for cell-type specific, tissue-specific, or inducible by external signals or agents; such elements may be located in the 5' or 3' regions of the of the polynucleotide sequence. Both constitutive and inducible promoters, are included in the invention (see e.g., Bitter et al., Methods in Enzymology 153:516–544, 1987). For example, when cloning in bacterial systems, inducible promoters such aspL of bacteriophage, plac, ptrp, ptac (ptplac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

The term "isolated" means altered "by the hand of man" from its natural state; ie., if it occurs in nature, it has been changed or removed from its original environment, or both For example, a naturally occurring polynucleotide or a polypeptide naturally present in a living animal in its natural state is not "isolated", but the same polynucleotide or polypeptide separated from the coexisting materials of its natural state is "isolated", as the term is employed herein. As part of or following isolation, a polynucleotide can be joined to other polynucleotides, such as for example DNAs, for mutagenesis studies, to form fusion proteins, and for propagation or expression of the polynucleotide in a host, or for gene therapy. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions). For example, a polynucleotide encoding a GST protein (e.g, GSTP1) can be operatively linked to a promoter and delivered to a subject or cell having a cell proliferative disorder associated with reduced expression of a GST or GSTP1.

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector, into an autonomously replicating plasmid or virus; or into the genomic DNA of a prokaryote or eukaryote, or which exists as a separate molecule (e.g., a CDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, a polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

Nucleic acid sequences can be created which encode a fusion protein and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences.

The invention provides a method for detecting a cell expressing GSTP1 or a cell proliferative disorder associated with GSTP1 in a tissue of a subject. The method includes contacting a target cell containing a GSTP1 nucleic acid or protein (a target cell component) and suspected of having a GSTP1 associated disorder, with a reagent which binds to the nucleic acid or protein The target cell component can be nucleic acid, such as DNA or RNA, or protein. When the component is nucleic acid, the reagent is a nucleic acid probe or PCR primer. When the cell component is protein, the reagent is typically an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the antibody, or will be able to ascertain such, using routine experimentation.

A number of methods exist for detection of methylated cytosine and can be used in the methods described herein (see, for example, U.S. Pat. Nos. 5,756,668; 5,786,146; 5,856,094; and 5,922,590, all of which are incorporated herein by reference in their entirety). For example, traditional methods depend upon cleavage of the phosphodiester bond alongside cytosine residues, using either methylation-sensitive restriction enzymes or reactive chemicals such as hydrazine which differentiate between cytosine and its 5-methyl derivative. Mapping of methylated regions in DNA has been performed using Southern hybridization approaches, based on the inability of methylation-sensitive restriction enzymes to cleave sequences which contain one or more methylated CpG sites. This method provides an assessment of the overall methylation status of CpG islands, including some quantitative analysis. A more sensitive method of detecting methylation patterns combines the use of methylation-sensitive enzymes and the polymerase chain reaction (PCR). After digestion of DNA with the enzyme, PCR will amplify from primers flanking the restriction site only if DNA cleavage was prevented by methylation. Another method that avoids the use of restriction endonucleases utilizes bisulfite treatment of DNA to convert all unmethylated cytosines to uracil. The altered DNA is amplified and sequenced to show the methylation status of all CpG sites.

Exemplary target regions to which PCR primers of the invention are designed include primers which flank the region that lies approximately −539 to −239 bp from the transcription start site of GSTP1, as described herein. As shown in Example 2 and Example 5, such primers can be designed to be specific for methylated regions of DNA if desired. For example, PCR primers (upstream primer, 5'-AGCCTGGGCCACAGCGTGAGACTACGT-3' (SEQ ID NO:1); downstream primer, 5'-GGAGTAAACAGACAGCAGGAAGAGGAC-3' (SEQ ID NO:2)) may be used to target a sequence approximately −539 to −239 bp from the transcription start site of GSTP1.

To selectively amplify GSTP1 promoter DNA containing $5\text{-}^{m}C$ in the "sense" strand, primers N-F1 (GenBank position 816–835, 5'-GTAATTTTTTTTTTTT TAAG-3' (SEQ ID NO:7)) and M-R1 (position 1405–1420, 5'-TAAAAACCGCTAACGA-3' (SEQ ID NO:8)) were included in the PCR reaction mixture; to amplify GSTP1 promoter DNA containing C in the "sense" strand, primers N-F1 and U-R1 (position 1406–1422 5'-CCTAAAAACCACTAACA-3' (SEQ ID NO:9)) were used. After heating to 94° C. for 2 min, PCR was conducted by incubation at 94° C. for 1 min, 44° C. for 2 min, and 72° C. for 3 min for 5 cycles, followed by incubation at 94° C. for 30 sec, 44° C. for 2 min, and 72° C. for 1.5 min for 25 cycles before a fin 72° C. for 6 min. Products from the first PCR reaction mixtures were subjected to a second round of "nested" PCR The second PCR reaction mixtures contained 1 µM of primers, 250 µM of deoxynucleotide triphosphates, and 1.25 units Taq polymerase in OptiPrime buffer #6 (Stratagene). To amplify GSTP1 promoter DNA containing $5\text{-}^{m}C$, primers M-F2 (position 897–918, 5'-TTTAGGGAATTTTTTTTCGCG-3' (SEQ ID NO:10)) and M-R2 (position 1327–1345, 5'-CCCTACCGA AAACCCGAAC-3' (SEQ ID NO:11)) were added to PCR reaction mixture; to amplify GSTP1 promoter DNA containing C, primers U-F2 (position 895–917, 5'-GGTTTTAGGGAATTTTTTTTGT-3' (SEQ ID NO:12)) and U-R2 (position, 1326–1346, 5'-ACCCTACCAAAAACCCAAAC-3' (SEQ ID NO:13)) were used. It should be understood that one of skill in the art can design primers to other regions of GSTP1, and the promoter region in particular.

Another method for detecting a methylated CpG-containing nucleic acid, includes contacting a nucleic acid-containing specimen with an agent that modifies unmethylated cytosine; amplifying the CpG-containing nucleic acid in the specimen by means of CpG-specific oligonucleotide primers; and detecting the methylated nucleic acid. It is understood that while the amplification step is optional, it is desirable.

The term "modifies" as used herein means the conversion of an unmethylated cytosine to another nucleotide which will distinguish the unmethylated from the methylated cytosine. Preferably, the agent modifies unmethylated cytosine to uracil. Preferably, the agent used for modifying unmethylated cytosine is sodium bisulfite, however, other agents that similarly modify unmethylated cytosine, but not methylated cytosine can also be used in the method of the invention. Sodium bisulfite ($NaHSO_3$) reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by Taq polymerase and therefore upon PCR, the resultant product contains cytosine only at the position where 5-methylcytosine occurs in the starting template DNA The primers used in the invention for amplification of a CpG-containing nucleic acid in the specimen, after bisulfite modification, specifically distinguish between untreated DNA, methylated, and non-methylated DNA. Methylation specific PCR (MSP) primers for the non-methylated DNA preferably have a T in the 3' CG pair to distinguish it from the C retained in methylated DNA, and the compliment is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with the 5' and 3' flanking sequences to hybridize therewith and permit amplification of the genomic locus.

Oligonucleotide primers of the invention are employed in the amplification process which is an enzymatic chain reaction that produces exponential quantities of target locus relative to the number of reaction steps involved. Typically, one primer is complementary to the negative (−) strand of the locus and the other is complementary to the positive (+) strand. Annealing the primers to denatured nucleic acid followed by extension with an enzyme, such as the large fragment of DNA Polymerase I (Klenow) and nucleotides, results in newly synthesized +and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof In one such automated embodiment, diethylphosphoramidites are used as starting materials and may be synthesized as described by Beaucage, et at. (Tetrahedron Letters, 22:1859–1862, 1981). One method for synthesizing oligonucleotides on a modified solid support is described in U.S. Pat. No. 4,458,066.

Any nucleic acid specimen, in purified or non-purified form, can be utilized as the starting nucleic acid or acids, provided it contains, or is suspected of containing, the specific nucleic acid sequence containing the target locus (e.g., CpG). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing specimen used for detection of methylated CpG may be from any source including colon, blood, lypmthatic and hepatic tissue and may be extracted by a variety of techniques such as that described by Maniatis, et al. (Molecular Cloning: A Laboratory Manual, Cold Spring Harbor, N.Y., pp 280, 281, 1982).

If the extracted sample is impure (such as plasma, serunm, or blood or a sample embedded in parrafin), it may be treated before amplification with an amount of a reagent effective to open the cells, fluids, tissues, or animal cell membranes of the sample, and to expose and/or separate the strand(s) of the nucleic acid(s). This lysing and nucleic acid denating step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405–437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase 1, Klenow fragment of *E. coli* DNA polymerase I, T4 DNA polymerase, other available DNA polymerases, polymerase muteins, reverse transcriptase, and other enzymes, including heat-stable enzymes (e.g., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Typically, the method of amplifying is by PCR, as described herein and as is commonly used by those of ordinary skill in the art. Alternative methods of amplification have been described and can also be employed as long as the methylated and non-methylated loci amplified by PCR using the primers of the invention is similarly amplified by the alternative means.

The amplified products are preferably identified as methylated or non-methylated by sequencing. Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., BiolTechnology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229–237,1988).

Optionally, the methylation pattern of the nucleic acid can be confirmed by restriction enzyme digestion and Southern blot analysis. Examples of methylation sensitive restriction endonucleases which can be used to detect 5'CpG methylation include SmaI, SacII, EagI, MspI, HpaII, BstUI and BssHII, for example.

Since the present invention shows that a decreased level of GSTP1 transcription is often the result of hypermethylation of the GSTP1 polynucleotide sequence and/or expression control sequences (e.g., the promoter sequence), it may be desirable to determine whether the promoter is hypermethylated. Accordingly, the invention provides methods of detecting or diagnosing a cell proliferative disorder of hepatic tissue or cells by detecting methylation of the expression control or promoter region of GSTP1. Probes useful for detecting methylation of the promoter region of GSTP1 are useful in such diagnositic or prognostic methods. In addition, primers that flank or amplify the promoter nucleic acid sequence of GSTP1 are useful in detecting methylation of the promoter and thus the risk or occurrence of cell proliferative disorders. Probes and primers useful in the invention for the detection of hypermethylation of the expresson control or promoter sequences of GSTP1 include, for example, nucleic acids having a sequence as set forth in SEQ ID Nos: 1, 2, 7, 8, 9, 10, 11, 13 and combinations thereof Actively transcribed genes generally contain fewer methylated CGs than the average number in DNA. Hypermethylation can be detected by, for example, restriction endonuclease treatment and Southern blot analysis among others. Therefore, in a method of the invention, when the cellular component detected is DNA, restriction endonuclease analysis can be used to detect hypermethylation of the GSTP1 expression control sequence. Any restriction endonuclease that includes CG as part of its recognition site and that is inhibited when the C is methylated, can be utilized. Typically, the methylation sensitive restriction endonuclease is BssHII, MspI, or HpaII, used alone or in combination. Other methylation sensitive restriction endonucleases will be known to those of skill in the art.

For purposes of the invention, an antibody or nucleic acid probe specific for GSTP1 may be used to detect the presence of GSTP1 polypeptide (using antibody) or polynucleotide (using nucleic acid probe) in biological fluids or tissues. Oligonucleotide primers based on any coding sequence region in the GSTP1 sequence are useful for amplifying DNA, for example by PCR. Any specimen containing a detectable amount of polynucleotide or antigen can be used. A preferred sample of this invention is tissue of hepatic origin, for example, liver tissue. Preferably the sample contains hepatic cells. Alternatively, biological fluids such as bile, lymph fluid or blood may be used which may contain cells indicative of an GSTP1-associated cell proliferative disorder. The subject can be any animal having a hepatic organ including, for example, mice, rat, fish, bovine, porcine, canine, feline, equine, and primate species. Preferably the subject is human.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

The method for detecting a cell expressing GSTP1 of the invention or a cell proliferative disorder associated with an GSTP1, described above, can be utilized for detection of residual hepatic cancer or other malignancies in a subject in a state of clinical remission. Additionally, the method for detecting GSTP1 polypeptide in cells is useful for detecting a cell proliferative disorder by measuring the level of GSTP1 in cells expressing GSTP1 in a suspect tissue in comparison with GSTP1 expressed in normal cells or tissue. In addition, the methods of the invention can also be used in staging of a cell proliferative disorder. Using the method of the invention, GSTP1 expression can be identified in a cell and the appropriate course of treatment can be employed (e.g., sense gene therapy or drug therapy). The expression pattern of the GSTP1 of the invention may vary with the stage of malignancy of a cell, for example as seen with prostatic intraepithelial neoplasia (PIN) (McNeal, et al., Human Pathol., 17:64, 1986) therefore, a sample such as liver tissue can be screened with a panel of GSTP1-specific reagents (i.e., nucleic acid probes or antibodies to GSTP1) to detect GSTP1 expression and diagnose the stage of malignancy of the cell.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of GSTP1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

For purposes of the invention, GSTP1 may be detected by the monoclonal antibodies when present in biological fluids and tissues. Any sample containing a detectable amount of GSTP1 can be used. A sample can be a liquid such as bile, blood, or lymph and the like, or a solid or semi-solid such as tissues, feces, and the like, or, alternatively, a solid tissue such as those commonly used in histological diagnosis.

In performing the assays it may be desirable to include certain "blockers" in the incubation medium (usually added with the labeled soluble antibody). The "blockers" are added to assure that non-specific proteins, proteases, or antiheterophilic immunoglobulins to anti-GSTP1 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (e.g., nonspecific) antibodies of the same class or subclass (isotype) as those used in the assays (e.g. IgG1, IgG2a, IgM, and the like) can be used as "blockers". The concentration of the "blockers" (normally 1–100 $\mu g/\mu l$) may be important, in order to maintain the proper sensitivity yet inhibit any unwanted interference by mutually occurring cross reactive proteins in the specimen.

In using a monoclonal antibody for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the GSTP1 antigen for which the monoclonal antibodies are specific.

The concentration of detectably labeled monoclonal antibody which is administered should be sufficient such that the binding to those cells having GSTP1 is detectable compared to the background. Further, it is desirable that the detectably labeled monoclonal antibody be rapidly cleared from the circulatory system in order to give the best target-to-background signal ratio.

As a general rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulins either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In,. $^{97}$Ru, $^{67}$Ga, $^{68}$Ga, $^{72}$AS, $^{89}$Zr, and $^{201}$Tl.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

Monoclonal antibodies used in the method of the invention can be used to monitor the course of amelioration of GSTP1 associated cell proliferative disorder. Thus, by measuring the increase or decrease in the number of cells expressing GSTP1 or changes in GSTP1 present in various body fluids, such as bile or blood, it would be possible to determine whether a particular therapeutic regiment aimed at ameliorating the disorder is effective.

Various antibody types and derivatives are applicable to the diagnostic and treatment methods of the invention. Humanized monoclonal antibodies are produced by transferring mouse complementarity determining regions from heavy and light variable chains of the mouse immunoglobulin into a human variable domain, and then substituting human residues in the framework regions of the murine counterparts, The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA, 86:3833 (1989), which is hereby incorporated in its entirety by reference. Techniques for producing humanized monoclonal antibodies are described, for example, by Jones et al., Nature, 321:522 (1986); Riechmann et al., Nature, 332:323 (1988); Verhoeyen et al., Science, 239:1534 (1988); Carter et al., Proc. Nat'l Acad. Sci. USA, 89:4285 (1992); Sandhu, Crit. Rev. Biotech., 12:437 (1992); and Singer et al., J. Immunol., 150:2844 (1993), which are hereby incorporated by reference.

Antibodies of the invention also may be derived from human antibody fragments isolated from a combinatorial immunoglobulin library. See, for example, Barbas et al, Methods: A Companion to Methods in Enzymology, Vol. 2, page 119 (1991); Winter et al, Ann. Rev. Immunol. 12:433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet., 7:13 (1994); Lonberg et al., Nature, 368:856 (1994); and Taylor et al., Int. Immunol., 6:579 (1994), which are hereby incorporated by reference.

Antibody fragments of the invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated by reference in their entireties. See also Nisonhoff et al., *Arch. Biochem. Biophys,.* 89:230 (1960); Porter, Biochem. J., 73:119 (1959); Edelman et al., Methods in Enzymology, Vol. 1, page 422 (Academic Press 1967); and Coligan et al., at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al, *Proc. Nat'l Acad. Sci. USA,* 69:2659 (1972). Alternatively, the variable chains can be linked by an intermolecular disulfide bond or cross-linked by chemicals such as glutaraldehyde. See, e.g., Sandhu, supra. Preferably, the $F_v$ fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to Methods in Enzymology, Vol. 2, page 97 (1991); Bird et al., Science, 242:423 (1988); Ladner et al., U.S. Pat. No. 4,946,778; Pack et al., BioTechnology, 11:1271 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology, Vol. 2, page 106 (1991).

The present invention also provides a method for treating a subject with an GSTP1-associated cell proliferative disorder. In hepatic cancer, the GSTP1 nucleotide sequence is under-expressed as compared to expression in a normal cell, therefore, it is possible to design appropriate therapeutic or diagnostic techniques directed to this sequence. Thus, where a cell-proliferative disorder is associated with the expression of GSTP1 associated with malignancy, nucleic acid sequences that modulate GSTP1 expression at the transcriptional or translational level can be used. In cases when a cell proliferative disorder or abnormal cell phenotype is associated with the under expression of GSTP1, for example, nucleic acid sequences encoding GSTP1 (sense) could be administered to the subject with the disorder.

The term "cell-proliferative disorder" denotes malignant as well as non-malignant cell populations which often appear to differ from the surrounding tissue both morphologically and genotypically. Such disorders may be associated, for example, with absence of expression of GSTP1. Essentially, any disorder which is etiologically linked to expression of GSTP1 could be considered susceptible to treatment with a reagent of the invention which modulates GSTP1 expression.

The term "modulate" envisions the suppression of methylation of GSTP1 promoter or augmentation of other GST gene expression when GSTP1 is under-expressed. When a cell proliferative disorder is associated with GSTP1 expression, such methylation suppressive reagents as 5-azacytadine can be introduced to a cell. Alternatively, when a cell proliferative disorder is associated with under-expression of GSTP1 polypeptide, a sense polynucleotide sequence (the DNA coding strand) encoding the promoter region or the promoter operably linked to the structural gene, or GSTP1 polypeptide can be introduced into the cell.

The present invention also provides gene therapy for the treatment of cell proliferative disorders which are mediated by GSTP1. Such therapy would achieve its therapeutic effect by introduction of the appropriate GSTP1 polynucleotide which contains either a normal GSTP1 regulatory region alone or in combination with a GSTP1 structural gene (sense), into cells of subjects having the proliferative disorder. Alternatively, the GSTP1 structural gene could be introduced operably linked to a heterologous promoter, such as the GSTM, GSTA or other promoter. Delivery of sense GSTP promoter polynucleotide constructs can be achieved using a recombinant expression vector such as a chimeric virus or a colloidal dispersion system.

In some instances it may be advantageous to deliver and express a GST sequence locally (e.g., within a particular tissue or cell type). For example, local expression of a GST (e.g., GSTP1) within a hepatic cell or tissue can be performed to treat, modulate or ameliorate a cell proliferative disorder within a hepatic cell or tissue. The nucleic sequence may be directly delivered to the tissue or cells, for example. Such delivery methods are known in the art and include, for example, electroporation, viral vector delivery systems and direct DNA uptake.

For example, a nucleic acid constructs of the present invention will comprise nucleic acid molecules in a form suitable for uptake into target cells within a host tissue. The nucleic acids may be in the form of bare DNA or RNA molecules, where the molecules may comprise one or more structural genes, one or more regulatory genes, antisense strands, strands capable of triplex formation, or the like. Commonly, the nucleic acid construct will include at least one structural gene under the transcriptional and translational control of a suitable regulatory region. More usually, nucleic acid constructs of the present invention will comprise nucleic acids incorporated in a delivery vehicle to improve transfection efficiency.

One such delivery vehicles comprises viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. CIRC. RES. 71:1508–1517, 1992, the disclosure of which is incorporated herein by reference. A suitable adenovirus gene delivery is described in Rosenfeld et al. Science 252:431434, 1991, the disclosure of which is incorporated herein by reference. Both retroviral and adenovirus delivery systems are described in Friedman Science 244:1275–1281, 1989, and "The Development Of Human Gene Therapy," Ed. Theodore Friedmann, Cold Spring Harbor Laboratory Press, New York, 1999, the disclosures of which are also incorporated herein by reference.

A second type of nucleic acid delivery vehicle comprises liposomal transfection vesicles, including both anionic and cationic liposomal constructs. The use of anionic liposomes requires that the nucleic acids be entrapped within the liposome. Cationic liposomes do not require nucleic acid entrapment and instead may be formed by simple mixing of the nucleic acids and liposomes. The cationic liposomes avidly bind to the negatively charged nucleic acid molecules, including both DNA and RNA, to yield complexes which give reasonable transfection efficiency in many cell types. See, Farhood et al. Biochem. Biophys. Acta. 1111 :239–246, 1992, the disclosure of which is incorporated herein by reference. A typical material for forming liposomal vesicles is lipofectin which is composed of an equimolar mixture of dioleylphosphatidyl ethanolamine (DOPE) and dioleyloxypropyl-triethylammonium (DOTMA), as described in Felgner and Ringold, Nature 337:387–388, 1989, the disclosure of which is incorporated herein by reference.

It is also possible to combine these two types of delivery systems. For example, Kahn et al. (1992), supra., teaches that a retrovirus vector may be combined in a cationic DEAE-dextran vesicle to further enhance transformation efficiency. It is also possible to incorporate nuclear proteins into viral and/or liposomal delivery vesicles to even further improve transfection efficiencies. See, Kaneda et al. Science 243:375–378, 1989, the disclosure of which is incorporated herein by reference.

The promoter polynucleotide sequences used in the method of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs can be administered to a subject as drug therapy, alone or simultaneously with a sense promoter for GSTP1 or a sense promoter operably linked with the structural gene for GSTP1.

In another embodiment, a GSTP1 structural gene is operably linked to a tissue specific heterologous promoter and used for gene therapy. For example, a GSTP1 gene can be ligated to liver specific promoters (e.g., albumin promoters, α1 antitrypsin promoters), for expression of GSTP1 in hepatic tissue. Alternatively, the promoter for another GST gene can be linked to the GSTP1 structural gene and used for gene therapy.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GSTP1 sequence (including promoter region) of interest into the viral vector, along with another gene which encodes the ligand for a receptor on a specific target cell, for example, to render the vector target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GSTP1 sense or antisense polynucleotide. Target specific retroviral vectors can include a combination targeting proteins on the surface of the viral particle as well as tissue specific promoters to further allow only expression of the retroviral vector in the desired tissue.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA. transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

The vectors of the invention can be used to transform a host cell or a cell derived from a subject (e.g., ex vivo therapy). By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a DNA molecule encoding a GST polypeptide or a fragment thereof or which contains an expression control element of GSTP1.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a GST polypeptide and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and W138.

Mammalian cell systems which utilize recombinant viruses or viral elements to direct expression may be engineered. For example, when using adenovirus expression vectors, a polynucleotide encoding a GST polypeptide may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a GST polypeptide or a fragment thereof in infected hosts (e.g., see Logan & Shenk, Proc. Natl. Acad. Sci. USA, 81:3655–3659, 1984). Alternatively, the vaccinia virus 7.5K promoter may be used. (e.g., see, Mackett, et al., Proc. Natl. Acad. Sci. USA, 79:7415–7419, 1982; Mackett, et al., J. Virol. 49:857–864, 1984; Panicali, et al, Proc. Natl. Acad. Sci. USA 79:49274931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a GST (e.g., a GSTP1) gene in host cells (Cone & Mulligan, Proc. Natl. Acad. Sci. USA, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a GST polypeptide controlled by appropriate expression control elements (e.g., promoter, enhancer, sequences, transcription terminators, polyadenylation sites, etc.), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including, but not limited to, the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt- cells respectively. Also, anti-metabolite resistance can be used as the basis of selection for dhfr, which confers resistance to methotrexate (Wigler, et al, Proc. Natl. Acad. Sci. USA, 77:3567, 1980; O'Hare, et al, Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G418 (Colberre-Garapin, et al., J. Mol. Biol. 150:1, 1981); and hygro, which confers resistance to hygromycin (Santerre, et al, Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2difluoromethyl)-DL-ornithine, DFMO (McConlogue L., In: Current Communications in Molecular Biology, Cold Spring Harbor Laboratory, ed., 1987).

Accordingly, the methods of the invention have applicability to the treatement hepatic cell proliferative disorders in veterinary applications in addition to applicability in human subjects. The vectors or delivery vehicles can be optimized by the skilled artisan for application to various animals and species.

Another targeted delivery system for GSTP1 polynucleotide is a colloidal dispersion system. Colloidal dispersion systems include macromolecule complexes, nanocapsules, microspheres, beads, and lipid-based systems including oil-in-water emulsions, micelies, mixed micelies, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in avariety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting GSTP1 antibody-containing liposomes directly to the malignant tumor. Since the GSTP1 gene product may be indiscriminate with respect to cell type in its action, a targeted delivery system offers a significant improvement over randomly injecting non-specific liposomes. Preferably, the target tissue is hepatic tissue. A number of procedures can be used to covalently attach either polyclonal or monoclonal antibodies to a liposome bilayer. Antibody-targeted iiposomes can include monoclonal or polyclonal antibodies or fragments thereof such as Fab, or F(ab')$_2$, so long as they bind efficiently to an antigenic epitope on the target cells. Liposomes may also be targeted to cells expressing receptors for hormones or other serum factors.

In yet another embodiment, the invention envisions treating a subject with low levels of GSTP1 expression with a glutathione-S-transferase inducing agent. Stimulation of the other classes of GSTs may compensate for the deficiency in GSTP1. Such inducers include sulfofurain, oltipraz, as well as other substances known in the art (Prochaska, et al., Proc. Nat'l. Acad. Sci., U.S.A, 89:2394, 1992; Zhang, et al., Proc. Nat'l. Acad. Sci., U.S.A., 89:2399, 1992; Prestera, et al., Proc. Nat'l. Acad. Sci., U.S.A., 90:2965, 1993). Methylation of GSTP1 promoter polynucleotide can be inhibited in vitro or in vivo by treatment with 5-aza-cytidine, 5-aza-deoxycytidine or procainamide, for example. Other similar agents will be known to those of skill in the art.

The invention also relates to a medicament or pharmaceutical composition comprising a GSTP1 promoter polynucleotide or a GSTP1 or other GST promoter polynucteotide or GST polynucleotide. Where the polynucleotide is an expression control element (e.g., a promoter), the expression control element is operably linked to the GSTP1 or GST structural gene in a pharmaceutically acceptable excipient or medium wherein the medicament is used for therapy of GSTP1 associated cell proliferative disorders. In this embodiment, the expression of GST or GSTP1 overcomes the deficiencies of expression in the target cell or tissue.

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe which is or can be detectably labeled. Such probe may be a nucleic acid sequence specific for a GSTP1 promoter region. For example, oligonucleotide probes of the invention can be included in a kit and used for examining the presence of hypermethylated nucleic acid sequences in a sample containing a GST nucleic acid sequence. The kit may also contain a container comprising a reporter-means, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the mutant target sequence, this can be accomplished using oligonucleotide(s) that are primers for amplification. These oligonucleotide primers are based upon identification of the flanking regions contiguous with the target nucleotide sequence. Accordingly, the kit may contain primers useful to amplify and screening a promoter region of a GST (e.g., the pomoter region of GSTP1). Such primers include, for example, SEQ ID Nos.: 1, 2, 7, 8, 9, 10, 11, 12, 13 and combinations thereof The invention will now be described in greater detail by reference to the following non-limiting examples.

EXAMPLES

Hep3B HCC cells and HCC tissue specimens. Human Hep3B HCC cells (Aden DP. et al., *Nature* 2:615–616, 1979) were propagated in vitro in MEM growth medium (Mediatech) supplemented with 1.0 mM sodium pyruvate and 10% fetal calf serum (Gibco-BRL Life Technologies). Human Tsu-Prl PCA cells (Iizumi et al., J Urol 137:1304–1306, 1987) were cultivated in RPMI 1640 medium (Mediatech) with 10% fetal calf serum. Treatment of Hep3B and Tsu-Prl cells with the DNA methyltransferase inhibitor 5-aza-deoxycytidine (5-aza-dC; Sigma Chemical Company) was accomplished by incubation of growing cell cultures in complete growth medium containing the inhibitor. Human HCC tissue specimens were recovered from partial liver resection procedures for HCC performed at the National Cancer Center Hospital in Tokyo, Japan, with the approval of the institutional ethics committee. The specimens used for study were residual materials present after appropriate pathological diagnostic evaluations were completed. Clinical data for HCC cases, including serum studies for hepatitis virus infection, were abstracted from case records. Genomic DNA was isolated from Hep3B HCC cells, from HCC tissues and adjacent non-cancerous tissues, and from normal white blood cells as described in Lee et al., Cancer Epidemiol Biomarkers Prev 6:443–450, 1997; and Lee et al., Proc Natl Acad Sci USA 21:11733–11737, 1994.

Example 1

Assessment of GSTP1 expression. To detect GSTP1 polypeptides in HCC tissues, formalin-fixed, paraffin-embedded HCC tissue specimens were cut into tissue sections, deparaffinized, hydrated, and stained for the presence of GSTP1 polypeptides with specific rabbit antiserum (Oncor) using an immunoperoxidase technique (Vector Laboratories). For human cancer cell lines propagated in vitro, the expression of GSTP1 mRNA and GSTP1 polypeptides were assessed using Northern blot and immunoblot analyses.

Increased expression of the rat π-class GST, GST-P, stereotypically accompanies HCC pathogenesis in rat chemical carcinogenesis models. In contrast, human HCC specimens contain neoplastic cells apparently devoid of the human π-class GST, GSTP1. To determine whether diminished or absent GSTP1 expression by human HCC cells might be the result of somatic alterations affecting the GSTP1 gene, human Hep3B HCC cells propagated in vitro were assessed for GSTP1 polypeptide expression by immunoblot analysis using anti-GSTP1 antiserum and for GSTP1 mRNA expression by Northern blot analysis using a GSTP1 cDNA probe (FIG. 1B). Hep3B HCC cells failed to express either GSTP1 polypeptides or GSTP1 mRNA (FIG. 1). LNCaP PCA cells and MCF-7 breast carcinoma (BCA) cells, which also fail to express GSTP1 polypeptides, contain GSTP1 genes with abnormally hypermethylated "CpG islands". In contrast, "CpG island" sequences in GSTP1 genes present in a variety of normal tissues, including normal liver, are characteristically not hypermethylated, regardless of whether cells comprising the normal tissues express GSTP1 or not. By Southern blot analysis of Hep3B HCC DNA digested with the $^{5-m}$C-sensitive restriction endonuclease BssHII, abnormal GSTP1 "CpG island" hypermethylation was detected (FIG. 1A) reminiscent of the abnormal GSTP1 DNA hypermethylation present in LNCAP PCA cell DNA and in MCF-7 BCA cell DNA. In fact, all GSTP1 promoter alleles present in Hep3B HCC cells manifested abnormal DNA hypermethylation (FIG. 1A).

To ascertain whether the GSTP1 "CpG island" hypermethylation changes present in Hep3B HCC cell DNA were associated with transcriptional silencing of the GSTP1 gene, Hep3B HCC cells were exposed to 5-aza-dC, an inhibitor of DNA methyltransferases (DNMTs), for as long as 72 hours. Experiments demonstrated that GSTP1 mRNA expression by the Hep3B cells began to appear within 24 hours, but increased in abundance by 72 hours. As expected, after 72 hours, Southern blot analysis of DNA from 5-aza-dC-treated Hep3B cells disclosed the appearance of unmethylated GSTP1 promoter alleles (FIG. 1A). In addition, Northern blot analysis of RNA from Hep3B cells treated with 5-aza-dC for 72 hours revealed a reactivation of GSTP1 mRNA expression (FIG. 1B). Although the applicants are under no duty or obligation to explain the mechanism by which the invention works it is suspected that 5-aza-dC treatment most likely triggered GSTP1 expression in Hep3B HCC cells by undermining the maintenance of the abnormal GSTP1 "CpG island" methylation changes. When Tsu-Prl PCA cells, which contain unmethylated GSTP1 promoter alleles and express abundant GSTP1 mRNA, were treated with 5-aza-dC in a manner similar to that used to reactivate GSTP1 expression in Hep3B HCC cells, no modulation of GSTP1 expression was evident. These data indicated that GSTP1 "CpG island" hypermethylation changes present in Hep3B HCC cells result in an absence of GSTP1 expression.

Example 2

Detection of somatic GSTP1 "CpG island" DNA hypermethylation changes. DNA isolated from Hep3B cells before and after exposure to 5-aza-dC in vitro was assessed for GSTP1 "CpG island" DNA hypermethylation using Southern blot analysis. Purified DNAs were digested first with HindIII and EcoRI and then extensively with the $^{5-m}$C-sensitive restriction endonuclease BssHII. Digested DNAs were then electrophoresed on agarose gels, transferred to Zeta-Probe (DioRad) membranes, and then hybridized with $^{32}$P-labeled GSTP1 cDNA DNA isolated from Hep3B HCC cells and from HCC and adjacent non-neoplastic tissues was also subjected to analysis for GSTP1 "CpG island" DNA hypermethylation using a $^{5-m}$C-sensitive restriction endonuclease-polymerase chain reaction (PCR) strategy that permitted both detection of CpG dinucleotide methylation and simultaneous discrimination of maternal and paternal alleles in informative cases. PCR primers (upstream primer, 5'-AGCCTGGGCCACAGCGTGAGACTACGT-3' (SEQ ID NO:1); downstream primer, 5'-GGAGTAAACAGACAGCAGGAAGAGGAC-3' (SEQ ID NO:2)) targeting a sequence (approximately −539 to −239 bp from the transcription start site; see GenBank accession # X08058 (which is incorporated herein by reference in its entirety) in the 5' regulatory region of GSTP1, which included a polymorphic (ATAAA)$_n$ (SEQ ID NO:3) repeat sequence and two recognition sites for the $^{5-m}$C-sensitive restriction endonuclease HpaII and its isoschizomer MspI, were used to amplify DNA samples that had been left undigested, or had been extensively digested with HpaII or MspI. A previous report suggested that among genomic DNA from healthy Japanese, (ATAAA)$_n$ (SEQ ID NO:3) sequences of between 18–27 repeats in the 5' regulatory region of GSTP1 could be detected, with 23 (27.2%) and 24 (24.1%) repeats representing the most common GSTP1 alleles (Harada S et al., Hum Genet 93:223–224, 1994). In all, some 81.8% of healthy Japanese were found to be polymorphic for GSTP1 (ATAAA)$_n$ repeats. For the GSTP1 allele-specific "CpG island" methylation assay, DNA isolated from HCC and adjacent non-HCC tissues were left undigested, or were extensively digested with HpaII or MspI before being subjected to PCK The 25 μl PCR mixture contained 20–100 ng sample DNA, 1.25 units Taq polymerase (Perkin-Elmer Corporation), 1 μM of each oligonucleotide primer, 200 μM deoxynucleotide triphosphates, and 15% glycerol in OptiPrime buffer #10 (Stratagene). To facilitate detection of the PCR amplification products, the downstream primer was end-labeled with [γ-$^{32}$P]ATP (Amersham) using T4 polynucleotide kinase (New England BioLabs). PCR was conducted by incubation at 95° C. for 1 min, 63° C. for 3 min, and 72° C. for 1.5 min, for 30 cycles followed by a final extension at 72° C. for 8 min. PCR amplification products, ranging in size from 290 bp to 335 bp, were then subjected to electrophoresis on 6% polyacrylamide DNA sequencing gels containing 8 M urea at 60 W for 2.5 h Gels were subsequently mounted on filter paper (Whatman), dried, and then exposed to X-OMAT film (Kodak).

Example 3

Analysis of GSTP1 expression and GSTP1 "CpG island" DNA hypermethylation in human HCC cells in vivo. To discover whether GSTP1 "CpG island" hypermethylation changes were responsible for absence of GSTP1 expression in human HCC cells in vivo, a series of 20 HCC tissue specimens were subjected to analysis for GSTP1 polypeptide expression by immunohistochemical staining using anti-GSTP1 antiserum and to analysis for GSTP1 "CpG island" DNA hypermethylation. In each tissue specimen, liver tissue adjacent to HCC lesions displayed characteristic morphological changes of hepatitis and cirrhosis. Although bile duct cells in normal liver tissues tend to express abundant GSTP1, normal hepatocytes generally fail to express GSTP1. In the HCC case series, even though the liver tissues adjacent to HCC displayed morphological changes of hepatitis and cirrhosis, the bile duct cells stained positively for GSTP1 while the hepatocytes failed to stain positively. In 19 of 20 HCC cases examined, HCC cells appeared devoid of GSTP1 expression (Table I). One of the HCC cases (case 1) appeared to contain rare cells which stained positively for GSTP1 amongst a larger number (>95%) of HCC cells which stained negatively for GSTP1.

TABLE I

GSTP1 expression and GSTP1 "CG island" methylation in 20 HCC cases.

| case number | age | sex | anti-GSTP1 immunostaining[a] | GSTP1 "CG island" DNA methylation[b] |
|---|---|---|---|---|
| 1 | 49 | F | negative/rare positive[c] | 2 of 2 alleles |
| 2 | 61 | M | negative | 2 of 2 alleles |
| 3 | 61 | M | negative | 1 of 2 alleles |
| 4 | 59 | M | negative | yes |
| 5 | 65 | M | negative | 2 of 2 alleles |
| 6 | 62 | M | negative | 2 of 2 alleles |
| 7 | 60 | M | negative | 2 of 2 alleles |
| 8 | 71 | M | negative | 1 of 2 alleles |
| 9 | 59 | M | negative | no |
| 10 | 64 | M | negative | yes |
| 11 | 44 | M | negative | no[d] |
| 12 | 60 | M | negative | 1 of 2 alleles |
| 13 | 73 | F | negative | 1 of 2 alleles |
| 14 | 69 | M | negative | 2 of 2 alleles |
| 15 | 72 | M | negative | 1 of 2 alleles |
| 16 | 68 | F | negative | yes |
| 17 | 68 | M | negative | 2 of 2 alleles |
| 18 | 72 | M | negative | 2 of 2 alleles |
| 19 | 49 | M | negative | no |
| 20 | 24 | F | negative | yes |

Figure 2:
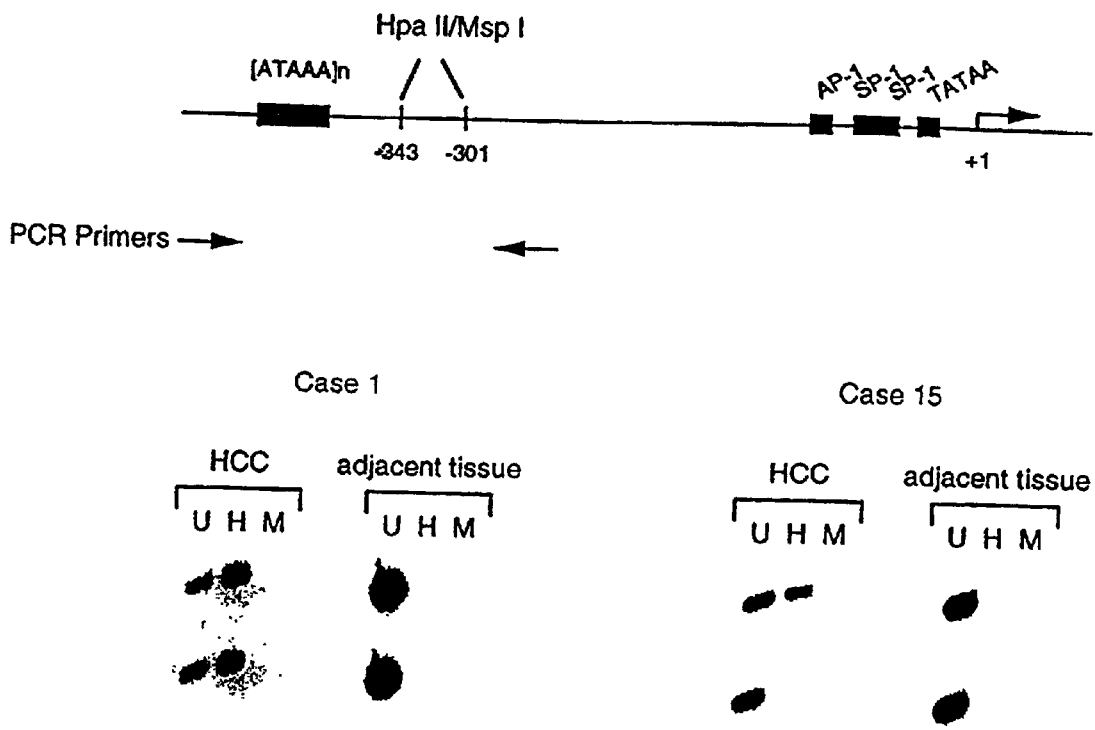
FIG. 2 shows the detection of GSTP1 'CpG island' methylation changes in HCC DNA using a PCR assay capable of discriminating CpG dinucleotide methylation changes affection maternal and paternal GSTP1 alleles. PCR primers (arrows); U, untreated; H, HpaII treated; M, MspI treated.

[a]Immunohistochemical staining for GSTP1 polypeptides was accomplished as described for FIG. 1.
[b]The presence of GSTP1 "CpG island" methylation was assayed using PCR as described for FIG. 2. For cases 4, 10, 16, and 20, only one GSTP1 allele could be discriminated. Among cases with two GSTP1 alleles discriminated, no allelic losses were evident.
[c]For case 1, GSTP1 polypeptides were detected in a small fraction of the cells (<5%) comprising the HCC.
[d]For case 11, GSTP1 "CpG island" DNA methylation was not detected HCC DNA, but was detected in 1 of 2 alleles in DNA from adjacent liver tissue. GSTP1 "CpG island" DNA methylation was not evident in DNA from liver tissue adjacent to HCC for any of the other cases.

To determine whether the absence of GSTP1 polypeptide expression in HCC cells in vivo might be accompanied by somatic GSTP1 "CpG island" hypermethylation, the methylation status of CpG dinucleotides present in HpaII/MspI sites located at −343 bp and −301 bp upstream of the transcription start site of GSTP1 in DNA from the 20 HCC specimens were surveyed using a PCR approach targeting a region (from −535 bp to −239 bp) encompassing a polymorphic (ATAAA)$_n$ repeat sequence. In informative cases, this assay allowed detection of GSTP1 "CpG island" hypermethylation affecting both the maternal and paternal alleles. Representative results of the application of this assay to the analysis of somatic GSTP1 DNA hypermethylation are displayed in FIG. 2. The appearance of PCR products following HpaII digestion of HCC DNA, but not of DNA from adjacent non-cancerous tissues, indicated that somatic GSTP1 "CpG island" DNA hypermethylation changes were likely present (FIG. 2). The absence of PCR products following MpI digestion of HCC DNA provided further evidence that the somatic alterations likely involved CpG dinucleotide hypermethylation at the HpaII/MspI recognition sites and not mutation. The results obtained from analysis of each of the 20 HCC cases studied are presented in Table I. None of the HCC cases for which maternal and paternal GSTP1 alleles could be discriminated showed loss of GSTP1 alleles. In one case (case 11), non-cancerous liver tissue DNA appeared to manifest CpG dinucleotide hypermethylation at the two HpaII/MspI sites in the GSTP1 "CpG island" targeted by the PCR assay used. DNA from 17 of 20 HCC specimens (85%) showed somatic hypermethylation changes present in at least 1 GSTP1 allele. DNA from 8 HCC specimens contained somatic hypermethylation changes in both paternal and maternal GSTP1 alleles (8 of 17 informative cases or 47%); DNA from 6 HCC specimens appeared to contain abnormal hypermethylation affecting one GSTP1 allele but not the other (6 of 17 informative cases or 35%).

Example 4

HBV DNA detection. HBV DNA (HBV complete genome; GenBank accession # X98077) was detected as described in Zhou et al., Cancer Res 57:2749–2753, 1997. PCR primers (upstream primer, position 3073–3089, 5'-GGGTGGAGCCCTCAGGCTCAGGGC-3' (SEQ ID NO:4); downstream primer, position 410–433, 5'-GAAGATGAGGCATAGCAGAC GGAT-3' (SEQ ID NO:5)) were used to amplify HBV DNA sequences in reaction mixtures containing 50 ng sample DNA, 1.25 units Taq polymerase, 1 µM each primer, 250 µM deoxynucleotide triphosphates. After initially heating the reaction mixtures to 95° C. for 5 min, PCR was conducted by incubation at 94° C. for 30 sec, 53° C. 35 sec, and 72° C. for 65 sec, for 30 cycles. PCR products were then separated by electrophoresis on 1% agarose gels, transferred to Zeta-Probe (Biorad) membranes, and hybridized with $^{32}$P-end-labeled oligonucleotide HBV DNA probes (position 54–69, 5'-TTCCTGCTGGTGGCTC-3' (SEQ ID NO:6)).

Figure 3:
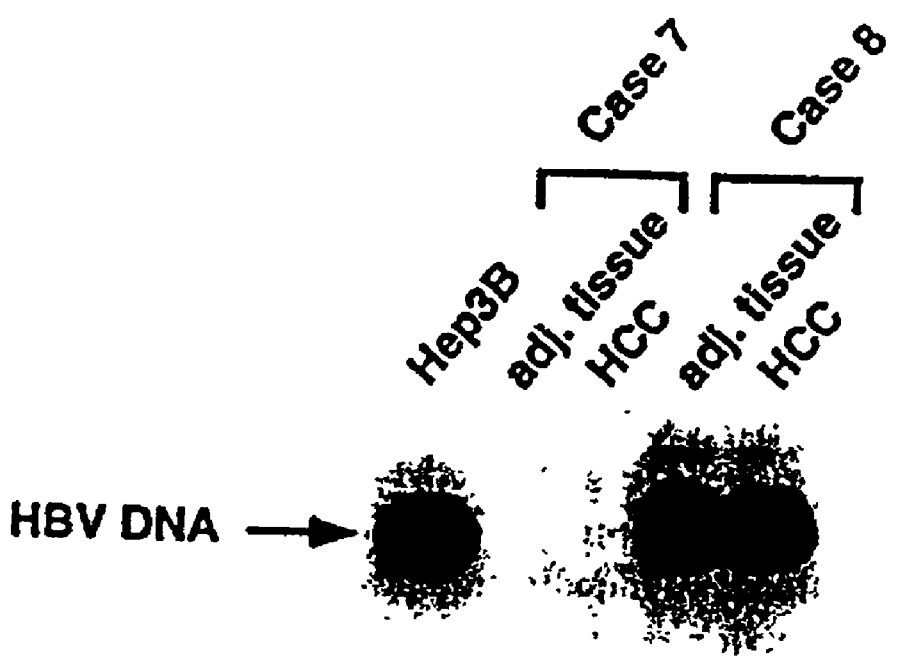
FIG. 3 shows the detection of hepatitis B virus DNA in DNA from HCC and DNA from tissues adjacent to HCC. The presence of HBV DNA sequences was monitored as the appearance of the predicted PCR product (arrow).

Zhou et al. reported that GST expression was significantly reduced in HCC cells when HBV DNA was present. Serum studies for HBV and HCV infection for each of the HCC cases are summarized in Table II. For all but one of the cases (case 6), serum studies indicated a history of HBV infection (12 cases), of HCV infection (11 cases), or of infection with both HBV and HCV (4 cases). Of cases with a history of HBV infection, HCC DNA displayed evidence of GSTP1 CG island methylation in 9 of 12 cases (75%). For cases with a history of HCV infection, GSTP1 CG island DNA methylation was detected in HCC DNA in 10 of 11 cases (91%). (To discern whether active HBV infection might contribute to the absence of GSTP1 expression in the 20 HCC cases examined in the study, HCC DNA and matched DNA from adjacent liver tissues was subjected to analysis for HBV infection using PCR technique. Representative results are shown in FIG. 3. Hep3B HCC cells are known to harbor HBV DNA. Thus, as expected, HBV DNA was readily detected by PCR as a single 572 bp product in Hep3B HCC DNA (FIG. 3, lane 1). HBV DNA was not detected in either HCC DNA or DNA from adjacent liver tissue in one representative HCC case (case 7; FIG. 3, lanes 2 and 3). HBV DNA was clearly present in DNA from both HCC and adjacent tissue in another representative HCC case (case 8; FIG. 3, lanes 4 and 5). Assay results for each of the 20 HCC cases are summarized in Table 2. 10 of 20 HCC cases had detectable HBV DNA among genomic DNA from either HCC tissue or from adjacent tissue. HBV DNA was occasionally detected in DNA from HCC tissue but not in DNA from adjacent tissue (cases 6 and 9) or vice versa (cases 4 and 13). HBV infection did not appear to cause GSTP1 "CpG island" hypermethylation. Abnormal GSTP1 promoter DNA hypermethylation was present in HCC DNA in 7 of 10 cases (70%) in which HBV DNA was present and in 10 of 10 cases (100%/) in which HBV DNA was not detected.

TABLE II

Hepatitis virus infection in the 20 HCC cases.

| case number | HBsAg | HBsAb | HBcAb | HBeAg | HBeAb | HCVAb | HBV DNA[a] |
|---|---|---|---|---|---|---|---|
| 1 | + | − | + | − | + | − | + (HCC and adj. tissue) |
| 2 | − | − | − | − | − | + | − |
| 3 | − | − | + | − | + | + | − |
| 4 | − | − | + | − | + | − | + (adj. tissue only) |
| 5 | − | − | − | − | − | − | − |
| 6 | − | − | − | − | − | + | + (HCC only) |
| 7 | − | − | − | − | − | + | − |
| 8 | + | − | + | − | + | − | + (HCC and adj. tissue) |
| 9 | − | + | + | − | + | + | + (HCC only) |
| 10 | − | − | − | − | − | + | − |
| 11 | − | + | + | − | + | − | + (HCC and adj. tissue) |
| 12 | − | − | − | − | − | + | − |
| 13 | + | − | − | − | + | − | + (adj. tissue only) |
| 14 | − | − | + | − | + | + | − |
| 15 | − | − | + | − | + | − | − |
| 16 | + | − | + | − | + | − | + (HCC and adj. tissue) |
| 17 | − | − | − | − | − | + | − |
| 18 | − | − | − | − | − | + | − |
| 19 | − | − | + | − | + | − | + (HCC and adj. tissue) |
| 20 | + | − | + | − | + | − | + (HCC and adj. tissue) |

[a]The presence of HB virus DNA in DNA isolated from HCC tissue and adjacent liver tissue was assayed by PCR as described for FIG. 2.

Example 5

Mapping of somatic GSTP1 "CpG Island" DNA hypermethylation changes by genomic sequencing after bisulfite treatment. For 12 of the HCC cases, sufficient genomic DNA was available from HCC tissues and from tissues adjacent to HCC to permit an attempt at fine mapping of GSTP1 "CpG island" DNA hypermethylation changes. The use of the bisulfite reaction and PCR to discriminate $^{5-m}$C from C in genomic DNA was described by Clark et al. (Nucleic Acids Res 22:2990–2997, 1994). To map $^{5-m}$C nucleotides in the GSTP1 gene promoter in HCC DNA, the procedure described by Clark et al. was employed with only minor modifications. 200 ng of genomic DNA isolated from normal and neoplastic liver cells and tissues were treated with EcoRI, mixed with 2 µg salmon sperm DNA (Sigma Chemical Company), and then treated with sodium bisulfite. Bisulfite-treated DNA was then subjected to 2 rounds of PCR. The first PCR reaction mixtures contained 100 ng of bisulfite-treated DNA, 1 µM of primers, 250 µM of deoxynucleotide triphosphates, and 1.25 units Taq polymerase in OptiPrime buffer #1 (Stratagene). To selectively amplify GSTP1 promoter DNA containing $^{5-m}$C in the "sense" strand, primers N-F1 (GenBank position 816–835, 5'-GTAATTTTTTTTTTTT TAAG-3' (SEQ ID NO:7)) and M-R1 (position 1405–1420, 5'-TAAAAACCGCTAACGA-3' (SEQ ID NO:8)) were included in the PCR reaction mixture; to amplify GSTP1 promoter DNA containing C in the "sense" strand, primers N-F1 and U-R1 (position 1406–1422 5'-CCTAAAAACCACTAACA-3' (SEQ ID NO:9)) were used. After heating to 94° C. for 2 min, PCR was conducted by incubation at 94° C. for 1 min, 44° C. for 2 min, and 72° C. for 3 min for 5 cycles, followed by incubation at 94° C. for 30 sec, 44° C. for 2 min, and 72° C. for 1.5 min for 25 cycles before a final extension at 72° C. for 6 min. Products from the first PCR reaction mixtures were subjected to a second round of "nested" PCP, The second PCR reaction mixtures contained 1 μM of primers, 250 μM of deoxynucleotide triphosphates, and 1.25 units Taq polymerase in OptiPrime buffer #6 (Stratagene). To amplify GSTP1 promoter DNA containing $^{5-m}C$, primers M-F2 (position 897–918, 5'-TTTTAGGGAATTTTTTTTCGCG-3' (SEQ ID NO:10)) and M-R2 (position 1327–1345, 5'-CCCTACCGA AAACCCGAAC-3' (SEQ ID NO:11)) were added to PCR reaction mixture; to amplify GSTP1 promoter DNA containing C, primers U-F2 (position 895–917, 5'-GGTTTTAGGGAATTTTTTTTTGT-3'(SEQ ID NO:12)) and U-R2 (position, 1326–1346, 5'-ACCCTACCAAAAACCCAAAC-3' (SEQ ID NO:13)) were used. Following heating to 94° C. for 3 min, PCR was conducted by incubation at 94° C. for 30 sec, 58° C. for 2 min, and 72° C. for 1.5 min for 30 cycles with a final extension at 72° C. for 6 min. To permit DNA sequencing, PCR products were purified by separation using low melting temperature agarose gel electrophoresis, isolated from the agarose (using a QIAquick gel extraction kit; Qiagen), and then recovered by ethanol precipitation with linear acrylamide (Ambion) as a carrier. Purified PCR products were subjected to direct DNA sequence analysis using a cycle sequencing approach with dye-labeled terminators (ABI PRISM™ Dye Terminator Cycle Sequencing Ready Reaction Kit, Perkin Elmer). DNA sequence ladders were analyzed using an ABI automated sequencer. The forward sequencing primer used was (position 1005–1021) 5'-TGGGAAAGAGGGAAAGG-3' (SEQ ID NO:14). The reverse sequencing primer used was (position 1280–1295) 5'-CTCTAAACCCCATCCC-3' (SEQ ID NO:15).

Although diminished or absent GSTP1 polypeptide expression was found for nearly all of HCC cases surveyed in the study, HCC DNA from only 50% of informative cases (8 of 16) displayed CpG dinucleotide hypermethylation at both maternal and paternal GSTP1 alleles at HpaII/MspI sites located –343 bp and –301 bp upstream of the GSTP1 transcription start site (see Table I). The other cases likely had GSTP1 alleles displaying hypermethylation at CpG dinucleotides at other sites. To ascertain whether different patterns of GSTP1 "CpG island" DNA hypermethylation changes might be present in different HCC cases, genomic sequencing analyses of bisulfite-treated DNA specimens were performed on DNA from Hep3B HCC cells and 13 HCC cases. The genomic sequencing strategy employed involved bisulfite treatment of genomic DNA followed by 2 rounds of PCR. For PCR amplifications, oligonucleotide primers specific for either the bisulfite reaction products of methylated GSTP1 target DNA sequences or for the bisulfite reaction products of unmethylated sequences were used. GSTP1 "DNA methylation-specific" primers generated PCR products using DNA from Hep3B HCC cells and from 9 of 12 (75%) HCC specimens (see FIGS. 4 and 5). No PCR products were generated using DNA from normal white blood cells. Examination of the distribution of methylated CpG dinucleotides throughout the GSTP1 promoter region in Hep3B cells indicated that all CpG dinucleotides located between –195 bp and +35 bp of the transcription start site contained $^{5-m}C$. DNA from the HCC cases exhibited a significant heterogeneity of CpG dinucleotide methylation patterns. Unfortunately, unlike the GSTP1 "CpG island" methylation assay featured in FIG. 2 and Table 1, the GSTP1 "CpG island" bisulfite genomic sequencing strategy used in FIGS. 4 and 5 did not permit selective assessment of CpG dinucleotide methylation patterns on maternal and paternal alleles. Rather, the GSTP1 "CpG island" bisulfite genomic sequencing assay, which subjected GSTP1 "CpG island" PCR products to direct DNA sequence analysis, was biased to detect the most prevalent CpG dinucleotide patterns in each DNA specimen. Nonetheless, more extensive CpG dinucleotide hypermethylation was present in HCC DNA than in DNA from adjacent liver tissues (FIG. 5). Of the 9 HCC DNA specimens that generated "DNA methylation-specific" PCR products, methylation of greater than 50% of the CpG dinucleotides between –195 bp and +35 bp of the transcription start site were seen in 7 HCC cases. Methylated CpG dinucleotides present in the region –80 bp to +35 bp containing the core transcriptional promoter for GSTP1 were evident in each of the 9 (100%) HCC cases. In contrast, methylated CpG dinucleotides located at –140 bp and at –100 bp were detected in only 3 of 9 (33%/) HCC cases. GSTP1 "DNA methylation-specific" PCR products were also detected in DNA isolated from tissues adjacent to HCC tissue in 3 of 11 (27%) HCC cases (see FIGS. 4 and 5). For one case (case 15), the pattern of CpG dinucleotide hypermethylation in the GSTP1 regulatory region in DNA from tissue adjacent to HCC resembled the CpG dinucleotide methylation pattern discerned for DNA from HCC tissue. These CpG dinucleotide hypermethylation changes in the DNA from adjacent tissue may have been present in non-neoplastic hepatocytes, or may have been present in HCC cells infiltrating the adjacent tissue. In another case (case 10), the GSTP1 regulatory region CpG dinucleotide hypermethylation patterns in HCC DNA and in adjacent tissue DNA were substantially different, suggesting that significant CpG dinucleotide hypermethylation changes were likely present in non-neoplastic hepatocytes. Of interest, in this case each of the CpG dinucleotide hypermethylation changes in DNA from tissue adjacent to HCC was also present in HCC DNA; however, the HCC DNA exhibited more extensive CpG hypermethylation changes. In a third case (case 11), extensive GSTP1 "CpG island" hypermethylation changes were detected in DNA from non-neoplastic tissue but not in DNA from the adjacent HCC tissue.

Figure 4:
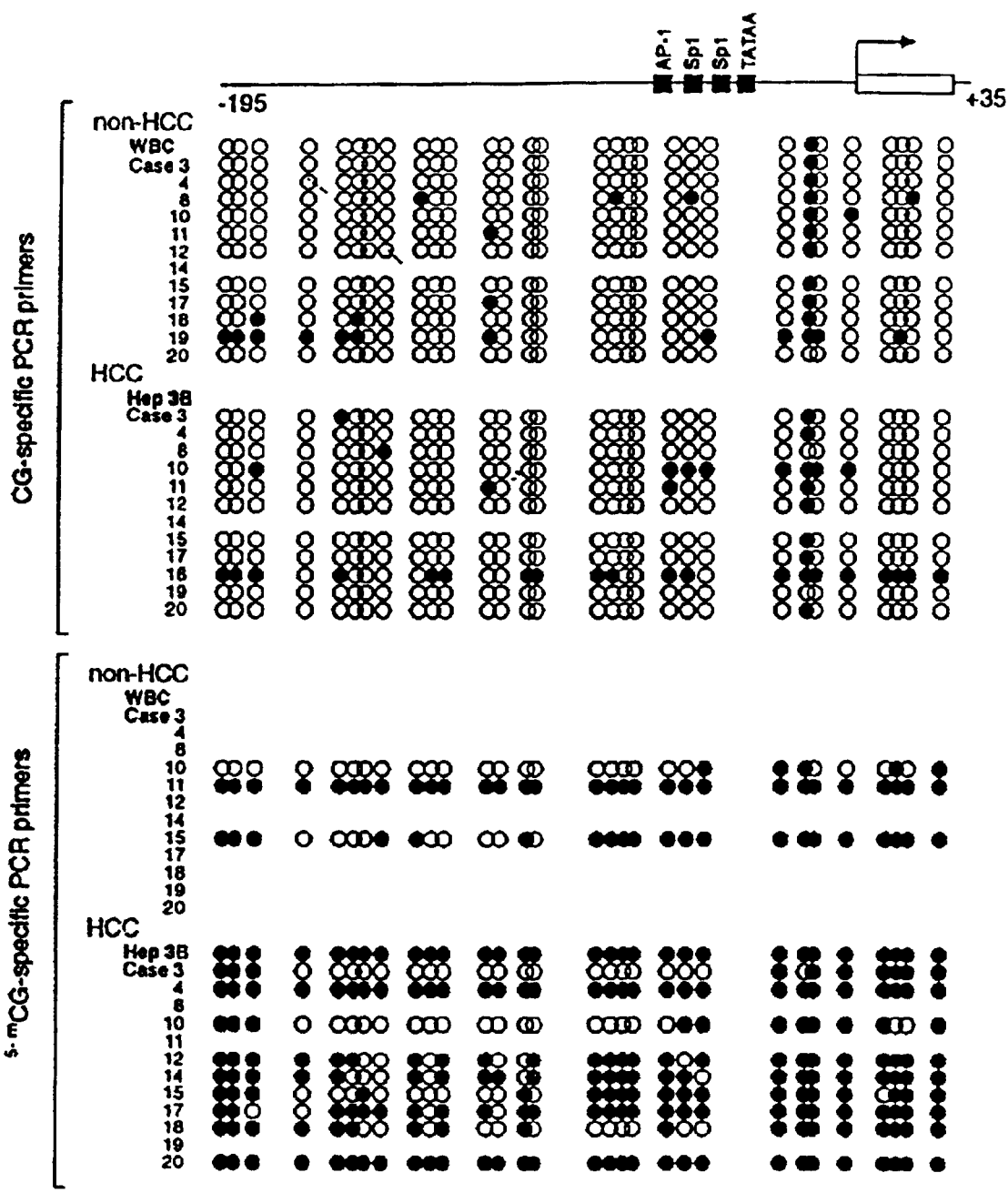
FIG. 4 shows the heterogeneity of GSTP1 "CpG island" DNA methylation changes in HCC DNA and in DNA from tissues adjacent to HCC revealed by bisulfite genomic sequencing. Results of bisulfite genomic sequencing analyses for $^{5-m}CpG$ dinucleotides located between −195 and +35 of the GSTP1 transcription start site using DNA prepared from HCC tissues and tissues adjacent to HCC are displayed. Two sets of PCR primers, one set specific for target sequences containing CpG dinucleotides and the other set specific for target sequences containing $^{5-m}CpG$ dincucleotides, were used to amplify bisulfite-treated DNA for DNA sequence analysis. Open circles designate CpG dinucleotides; closed circles designate $^{5-m}CpG$ dinucleotides. The absence of circles for some cases indicates failure of the PCR reaction to generate amplification products.
Figure 5:
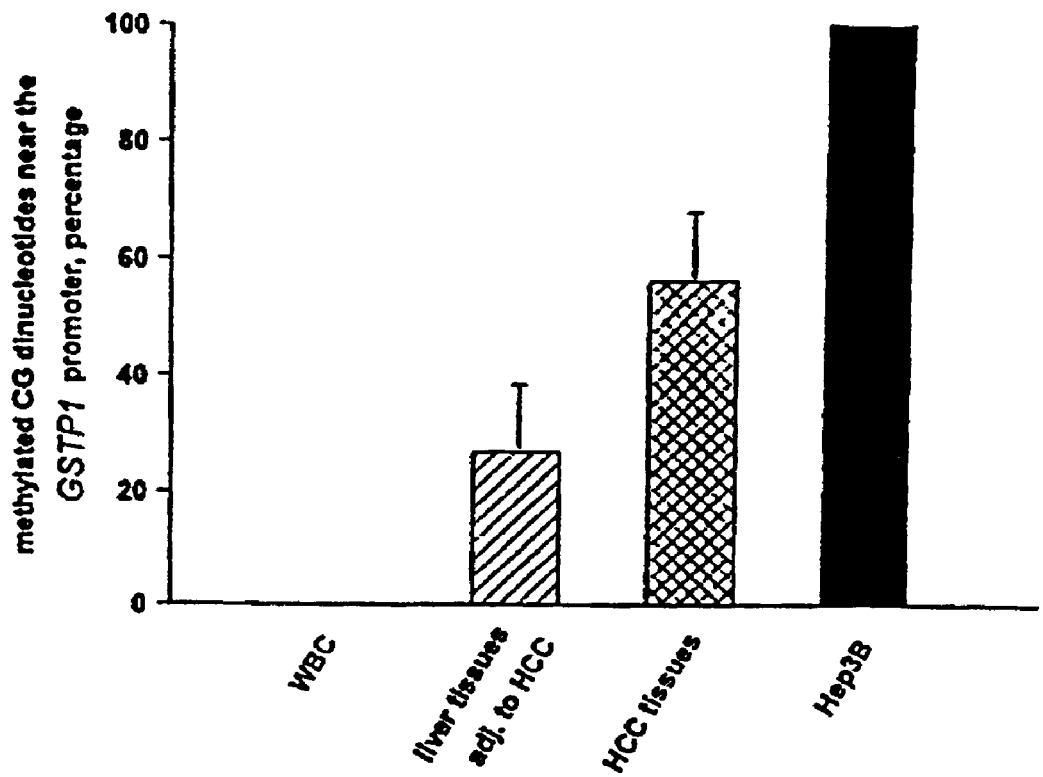
FIG. 5 shows the accumulation of GSTP1 "CpG island" DNA methylation changes during human hepatocarcinogenesis. The percentage of the 30 CpG dinucleotides located between nucleotides −195 and +35 of the transcriptional start site carrying $^{5-m}C$ instead of C was computed for each of the DNA specimens analyzed by bisulfite genomic sequencing in FIG. 4. For each CpG dinucleotide from each DNA specimen, the C nucleotide was scored as $^{5-m}C$ if the nucleotide appeared as $^{5-m}C$ in either of the 2 PCR reactions performed (using either $^{5-m}CpG$-specific-primers or CpG-specific primers). For HCC tissues and for liver tissues adjacent to HCC, the percentage of $^{5-m}CpG$ dinucleotides at the GSTP1 "CpG island" is displayed as the mean (for the 12 cases) +/− the standard error of the mean. Results of genomic sequencing analyses for normal white blood cells (WBC; 0.3%) and for Hep3B HCC cells (Hep3B; 100%) are also displayed.

PCR primers specific for unmethylated GSTP1 target sequences generated PCR products using DNA from normal white blood cells and from each of the HCC specimens (see FIGS. 4 and 5). No PCR products were generated using DNA from Hep3B HCC cells. The distribution of methylated CpG dinucleotides in the GSTP1 promoter region in normal white blood cells appeared restricted to a single CpG dinucleotide located at –15 bp from the transcriptional start site (FIG. 5). Similar CpG dinucleotide methylation patterns were detected in 4 of 11(36%) DNA specimens prepared from tissues adjacent to HCC (FIG. 5). For the remaining 7 of 11 (64%) cases, DNA isolated from tissues adjacent to HCC displayed abnormal CpG methylation patterns. PCR products generated from HCC DNA also displayed abnormal CpG dinucleotide methylation patterns in the GSTP1 regulatory region in 5 of 11 cases (46%; FIG. 5). For one such case (case 18), the abnormal CpG dinucleotide methylation patterns discriminated using PCR primers specific for methylated target sequences versus unmethylated target sequences were different (FIG. 4). Analysis of HCC DNA from this case using the HpaII-PCR assay capable of monitoring DNA hypermethylation in both maternal and paternal alleles had suggested that both alleles carried somatic DNA hypermethylation changes affecting GSTP1 regulatory region (Table I). The two CpG dinucleotide hypermethylation patterns discriminated using genomic sequence analysis of bisulfite-treated DNA are likely reflective of different somatic hypermethylation changes present in maternal versus paternal GSTP1 promoter alleles.

The genomic sequence analyses undertaken following bisulfite treatment of DNA from normal white blood cells, from Hep3B HCC cells, from HCC tissues, and from tissues adjacent to HCC, disclosed the presence of $^{5-m}$CCG and $^{5-m}$C$^{5-m}$CG trinucleotides at some sites in the GSTP1 regulatory region in addition to $^{5-m}$CG dinucleotides. $^{5-m}$C$^{5-m}$CG trinucleotides were present at −16 of the transcriptional start site in almost all normal and neoplastic DNA specimens examined. $^{5-m}$C$^{5-m}$CG trinucleotides were present at −148 bp and −77 bp of the transcription start site in Hep3B DNA and in 5 of 9 (56%) and 3 of 9 (33%/) HCC cases, respectively, but were absent from normal white blood cell DNA and from DNA isolated from tissues adjacent to HCC in 10 of 12 cases (83%) evaluable. No $^{5-m}$CAG or 5-mCTG trinucleotides were detected in any of the DNA specimens studied.

For a somatic genome alteration to target a critical gene for cancer pathogenesis, the alteration must be heritable through mitosis and affect gene function in a manner that permits cells containing the alteration to enjoy a selective growth advantage. CpG dinucleotide methylation patterns can be maintained through mitosis via DNA-MT action, and "CpG island" hypermethylation stereotypically affects gene function by preventing gene transcription. In general, in the absence of "CpG island" hypermethylation, genes may be transcribed or not transcribed subject to trans regulatory effects. In the presence of "CpG island" hypermethylation, genes can not be transcribed independent of trans regulatory influences. The invention demonstrates an absence of GSTP1 polypeptides in HCC cells in nearly all HCC cases evaluated. For many of the HCC cases analyzed, GSTP1 "CpG island" hypermethylation changes appeared to be present at both GSTP1 alleles, perhaps resulting in an absence of inducible GSTP1 activity.

Hep3B HCC cells propagated in vitro failed to express GSTP1 mRNA and contained only hypermethylated GSTP1 promoter alleles. When HCC cells were treated with the DNMT inhibitor 5-aza-dC, the appearance of unmethylated GSTP1 promoter alleles was accompanied by the appearance of detectable GSTP1 mRNA This result demonstrates that the GSTP1 "CpG island" hypermethylation changes were associated with GSTP1 silencing in Hep3B HCC cells in vitro and that similar GSTP1 DNA hypermethylation changes are associated with GSTP1 silencing in HCC cells in vivo. Studies of DNA methylation effects on the transcriptional regulation of several different genes have identified direct promoter silencing effects, resulting from interference of transcription factor binding to cis regulatory sequences (Watt F and Molloy P L, GenesDev 2:1136–1143, 1988; Bednarik D P et al., NewBiol 3:969–976,1991; Comb M and Goodman H M, Nucleic Acids Res 18:3975–3982, 1990; Singal R et al., Proc Natl Acad Sci USA 94:13724–13729, 1997; Prendergast G C et al., Cell 65:395–407, 1991; Prendergast G C and Ziff E B, Science 251:186–189, 1991), and indirect promoter repression effects, mediated through $^{5-m}$C binding proteins (Keshet I et al., Cell 44:535–543, 1986; Meehan R R et al., Cell 58: 499–507, 1989; Boyes J and Bird A, Cell 64:1123–1134, 1991; Boyes J and Bird A, Embo J 11: 327–333, 1992; Meehan R R et al., Nucleic Acids Res 20:5085–5092, 1992; Lewis J D et al., Cell 69:905–914, 1992; Nan X et al., Cell 88:471–481, 1997; Kudo S, Mol Cell Biol 18:5492–5499, 1998; Nan X, Nature 393: 386–389, 1998; Jones P L et al., Nat Genet 19:187–191, 1998). Indirect promoter repression effects have been reported to depend both on the density of CpG dinucleotide methylation and on promoter strength. Preliminary results of an analysis of the consequences of CpG dinucleotide methylation on GSTP1 promoter activity in MCF-7 BCA cells in vitro have indicated that direct promoter silencing effects may be sufficient for transcriptional inhibition (unpublished data). Whether similar mechanisms contribute to GSTP1 gene silencing in HCC cells has not been tested. Nonetheless, genome sequencing analyses of "CpG island" methylation changes in DNA from Hep3B HCC cells in vitro and from HCC tissues in vivo revealed fairly consistent CpG dinucleotide hypermethylation changes directly affecting the core GSTP1 promoter, despite a general heterogeneity in CpG dinucleotide hypermethylation changes throughout the GSTP1 "CpG island." Detailed promoter analyses may prove necessary to ascertain whether GSTP1 "CpG island" hypermethylation changes of the kind present in HCC tissues in vivo result in transcriptional inactivation via a direct or via an indirect promoter silencing mechanism.

GSTP1 "CpG island" hypermethylation, the most somatic common genome alteration yet reported in human PCA cells, appears to result in a crippling of inducible enzyme defenses against oxidant and electrophilic carcinogens. GSTP1 DNA hypermethylation changes have also been detected in the majority of PIN lesions thought to represent PCA precursors. These findings have formed the basis for a new model of prostatic carcinogenesis, in which prostatic cells with defective GSTP1 genes become vulnerable to oxidants and electrophiles tending to promote neoplastic transformation and PCA cells with defective GSTP1 genes remain vulnerable to similar stresses tending to promote malignant. If the pathogenesis of human HCC proceeds via a similar mechanism, a new model for human hepatocarcinogenesis can be proposed. In this model normal hepatocytes do not express GSTP1, but when cells are exposed to electrophilic or oxidant carcinogens, GSTP1 expression can be induced as a defense against genome damage. Hepatocytes that contain inactivated GSTP1 genes will be incapable of GSTP1 induction and will become vulnerable to genome damage inflicted by carcinogen exposure. Hepatocytes that acquire alterations in critical genes will be prone to undergo neoplastic transformation and tumor formation.

Our new model for human HCC pathogenesis can also be considered in comparison to previous mechanistic models and previous observations derived from studies of chemical hepatocarcinogenesis in rodents and other species. The hypothesis that a somatic deficiency in inducible GSTP1 activity in some human hepatocytes may confer carcinogen sensitivity is most reminiscent of hepatocarcinogenesis in different fish species, where liver tumor development may be facilitated by inadequate GST expression (Hayes M A et al., Sci Total Environ 94:105–123,1990; Kirby G M et al., Carcinogenesis 11: 2255–2257,1990). In addition, a possible reasons for the differences between GST-P expression during hepatocarcinogenesis in rodents and GSTP1 expression during hepatocarcinogenesis in humans may be (i) that hepatitis virus exposure and cirrhosis, which may be associated with diminished GST expression, constitute major etiological factors in human HCC development in the case series provided here while chemical carcinogen exposure constitutes the major etiological factor in HCC development in the various rodent model systems, (ii) that human GSTP1 gene may be regulated differently in hepatocytes than the rodent GST-P gene, and (iii) that the human GSTP1 gene may be more prone to suffer somatic de novo "CpG island" DNA hypermethylation during hepatocarcinogenesis than the rodent GST-P gene. In fact, a recent report suggests that hypomethylation at the GST-P gene may be more characteristic of rodent hepatocarcinogenesis (Steinmetz K L et al., Carcinogenesis 19:1487–1494, 1998). Thus, although a dysregulation of the fidelity of DNA methylation pattern maintenance may be characteristic of both human and rodent hepatocarcinogenesis, the resultant DNA methylation pattern changes appear distinct, complex, and likely affected by different selection pressures.

The findings of somatic GSTP1 defects associated with the pathogenesis of human HCC has significant implications both for the diagnosis and staging of HCC. PCR-based strategies targeting GSTP1 "CpG island" DNA hypermethylation changes, such as the assays presented in above or other assays useful for the detection of other cancer cells with similar GSTP1 "CpG island" hypermethylation changes, can be used to detect HCC DNA in liver biopsy tissues and in serum or plasma (78). GSTP1 "CpG island" hypermethylation detection provides a valuable molecular biomarker for HCC with clinical applications. In the present study, abnormal GSTP1 "CpG island" hypermethylation was detected in DNA from the majority of HCC cases regardless of the assay used (17 of 20 cases or 85% for the HpaII-PCR assay (see Table I) and a total of 10 of 12 cases or 83% for the bisulfite genomic sequencing assay (see FIG. 5)). HCC most commonly arises in the setting of chronic hepatitis and cirrhosis. Thus, the one strategy for detecting GSTP1 "CpG island" hypermethylation as a biomarker for HCC DNA will be an assay targeting the specific region of the GSTP1 "CpG island" most selectively hypermethylated in HCC DNA relative to DNA from liver tissue displaying hepatitis and cirrhosis.

While the invention has been described in detail with reference to certain preferred embodiments thereof, it will be understood that modifications and variations are within the spirit and scope of that which is described and claimed.

What is claimed is:

1. A method for detecting liver cancer in a human, comprising detecting hypermethylation of a CpG-containing promoter region at about nucleotide positions −539 to −239 or −195 to +35 of a glutathione-S-transferase P1 (GSTP1) gene transcription start site in a sample comprising nucleic acids from a hepatic tissue specimen, bile, or blood, wherein a hypermethylation of the CpG-containing promoter region is indicative of liver cancer.

2. The method of claim 1, wherein the hypermethylation of the promoter region is detected by contacting the nucleic acids with GSTP1 oligonucleotide primers.

3. The method of claim 2, wherein the primers flank the promoter region at about nucleotide positions −195 to +35 of the GSTP1 gene.

4. The method of claim 2, wherein the primers flank the promoter region at about nucleotide positions −539 to −239 of the GSTP1 gene.

5. The method of claim 2, wherein the nucleic acid primers are selected from the group consisting of SEQ ID NO:1, 2, 7, 8, 9, 10, 11, 12, 13, and combinations thereof.

6. The method of claim 1, wherein the detecting comprises contacting the nucleic acids with an agent that modifies nonmethylated cytosine residues, amplifying CpG-containing nucleic acids by means of CpG-specific oligonucleotide primers, wherein the oligonucleotide primers distinguish between modified methylated and nonmethylated nucleic acid, and detecting the methylated CpG-containing promoter region based on the presence or absence of amplification products produced in said amplifying step.

7. The method of claim 6, wherein the amplifying step comprises a polymerase chain reaction.

8. The method of claim 6, wherein the oligonucleotide primers have a sequence selected from the group consisting of SEQ ID NO: 7, 8, 9, 10, 11, 12, and 13.

9. The method of claim 6, wherein the modifying agent is bisulfite.

10. The method of claim 6, wherein cytosine is modified to uracil.

11. The method of claim 1, wherein the detecting comprises contacting the nucleic acids or a GSTP1 amplification product thereof with a methylation sensitive restriction endonuclease.

12. The method of claim 11, wherein the restriction endonuclease is selected from the group consisting of MspI, HpaII, BssHII, BstUI and NotI.

13. The method of claim 1, wherein the hypermethylation is detected by contacting the nucleic acids of the sample or a GSTP1 amplification product thereof, with a nucleic acid probe.

14. The method of claim 13, wherein the probe is detectably labeled.

15. The method of claim 14, wherein the label is selected from the group consisting of a radioisotope, a bioluminescent compound, a chemiluminescent compound, a fluorescent compound, a metal chelate, and an enzyme.

16. The method of claim 1, further comprising detecting the presence of hepatitis B virus or hepatitis C virus.

17. The method of claim 1, wherein hypermethylation is detected by comparing the methylation status of the promoter region at about nucleotide positions −539 to −239 or −195 to +35 of the GSTP1 gene to the methylation status of the promoter region in adjacent normal hepatic tissue.

18. A method for detecting liver cancer in a human, comprising contacting a target cellular component containing a nucleic acid with a reagent which reacts with a CpG-containing promoter region at about nucleotide positions −539 to −239 or −195 to +35 of a glutathione-S-transferase P1 (GSTP1) gene transcription start site and detecting hypermethylation of the CpG-containing promoter region, wherein hypermethylation of the promoter region is indicative of liver cancer.

19. The method of claim 18, wherein the reagent is a probe.

20. The method of claim 19, wherein the probe is an oligonucleotide probe.

21. The method of claim 19, wherein the probe is detectably labeled.

22. The method of claim 21, wherein the label is selected from the group consisting of a radioisotope, a bioluminescent compound, a chemiluminescent compound, a fluorescent compound, a metal chelate, or an enzyme.

23. The method of claim 18, wherein the reagent is a restriction endonuclease.

24. The method of claim 23, wherein the restriction endonuclease is methylation sensitive.

25. The method of claim 24, wherein the restriction endonuclease is selected from the group consisting of MspI, HpaII, BssHI, BstUI and NotI.

26. The method of claim 18, further comprising detecting the presence of hepatitis B virus or hepatitis C virus.

27. The method of claim 18, further comprising comparing the methylation status of the GST nucleic acid to the methylation status of the GST nucleic acid in adjacent normal hepatic tissue.

28. The method of claim 1 or claim 18, wherein methylation is in one allele.

29. The method of claim 1 or claim 18, wherein methylation is in both alleles.

30. The method of claim 1, wherein the liver cancer is hepatocellular carcinoma.

31. The method of claim 18, wherein the liver cancer is hepatocellular carcinoma.

32. The method of claim 1, wherein the CpG-containing promoter region is at about nucleotide positions −80 and +35 of the GSTP1 gene transcriptional start site.

33. The method of claim 18, wherein the CpG-containing promoter region is at about nucleotide positions −80 and +35 of the GSTP1 gene transcriptional start site.

34. The method of claim 1, wherein the CpG-containing promoter region is at about nucleotide positions −343 and −301 bp from the GSTP1 gene transcription start site.

35. The method of claim 18, wherein the CpG-containing promoter region is at about nucleotide positions −343 and −301 bp from the GSTP1 gene transcription start site.

* * * * *

SEQUENCE LISTING

<160> NUMBER OF SEQ ID NOS: 15

<210> SEQ ID NO 1
<211> LENGTH: 27
<212> TYPE: DNA
<213> ORGANISM: Artificial sequence
<220> FEATURE:
<223> OTHER INFORMATION: upstream primer targeting a piece of GenBank
      # X08058

<400> SEQUENCE: 1
agcctgggcc acagcgtgag actacgt                                      27

<210> SEQ ID NO 2
<211> LENGTH: 27
<212> TYPE: DNA
<213> ORGANISM: Artificial sequence
<220> FEATURE:
<223> OTHER INFORMATION: downstream primer targeting a piece of GenBank
      # X08058

<400> SEQUENCE: 2
ggagtaaaca gacagcagga agaggac                                      27

<210> SEQ ID NO 3
<211> LENGTH: 5
<212> TYPE: DNA
<213> ORGANISM: Artificial sequence
<220> FEATURE:
<223> OTHER INFORMATION: 5' regulatory region of GSTP1, polymorphic
      repeat sequence

<400> SEQUENCE: 3 ataaa                                                               5

<210> SEQ ID NO 4
<211> LENGTH: 24
<212> TYPE: DNA
<213> ORGANISM: Artificial sequence
<220> FEATURE:
<223> OTHER INFORMATION: upstream primer for piece of GenBank # X98077

<400> SEQUENCE: 4
gggtggagcc ctcaggctca gggc                                         24

<210> SEQ ID NO 5
<211> LENGTH: 24
<212> TYPE: DNA
<213> ORGANISM: Artificial sequence
<220> FEATURE:
<223> OTHER INFORMATION: downstream primer for piece of GenBank # X98077

<400> SEQUENCE: 5
gaagatgagg catagcagac ggat                                          24

<210> SEQ ID NO 6
<211> LENGTH: 16
<212> TYPE: DNA
<213> ORGANISM: Artificial sequence
<220> FEATURE:
<223> OTHER INFORMATION: HBV DNA probes

<400> SEQUENCE: 6
ttcctgctgg tggctc                                                   16

<210> SEQ ID NO 7
<211> LENGTH: 20
<212> TYPE: DNA
<213> ORGANISM: Artificial sequence
<220> FEATURE:
<223> OTHER INFORMATION: primer N-F1

<400> SEQUENCE: 7 gtaattttttt ttttttaag                                              20

<210> SEQ ID NO 8
<211> LENGTH: 16
<212> TYPE: DNA
<213> ORGANISM: Artificial sequence
<220> FEATURE:
<223> OTHER INFORMATION: Primer M-R1

<400> SEQUENCE: 8
taaaaaccgc taacga                                                   16

<210> SEQ ID NO 9
<211> LENGTH: 17
<212> TYPE: DNA
<213> ORGANISM: Artificial sequence
<220> FEATURE:
<223> OTHER INFORMATION: Primer U-R1

<400> SEQUENCE: 9
cctaaaaacc actaaca                                                  17

<210> SEQ ID NO 10
<211> LENGTH: 22
<212> TYPE: DNA
<213> ORGANISM: Artificial sequence
<220> FEATURE:
<223> OTHER INFORMATION: Primer M-F2

<400> SEQUENCE: 10
ttttagggaa ttttttttcg cg                                            22

<210> SEQ ID NO 11
<211> LENGTH: 19
<212> TYPE: DNA
<213> ORGANISM: Artificial sequence
<220> FEATURE:
<223> OTHER INFORMATION: Primer M-R2

-continued

```
<400> SEQUENCE: 11
ccctaccgaa aacccgaac                                                      19

<210> SEQ ID NO 12
<211> LENGTH: 23
<212> TYPE: DNA
<213> ORGANISM: Artificial sequence
<220> FEATURE:
<223> OTHER INFORMATION: Primer U-F2

<400> SEQUENCE: 12
ggttttaggg aattttttt tgt                                                  23

<210> SEQ ID NO 13
<211> LENGTH: 20
<212> TYPE: DNA
<213> ORGANISM: Artificial sequence
<220> FEATURE:
<223> OTHER INFORMATION: Primer U-R2

<400> SEQUENCE: 13
accctaccaa aaacccaaac                                                     20

<210> SEQ ID NO 14
<211> LENGTH: 17
<212> TYPE: DNA
<213> ORGANISM: Artificial sequence
<220> FEATURE:
<223> OTHER INFORMATION: forward sequencing primer

<400> SEQUENCE: 14
tgggaaagag ggaaagg                                                        17

<210> SEQ ID NO 15
<211> LENGTH: 16
<212> TYPE: DNA
<213> ORGANISM: Artificial sequence
<220> FEATURE:
<223> OTHER INFORMATION: reverse sequencing primer

<400> SEQUENCE: 15
ctctaaaccc catccc                                                         16
```